(12) United States Patent
Weiss

(10) Patent No.: US 9,079,975 B2
(45) Date of Patent: *Jul. 14, 2015

(54) INSULIN ANALOGUES WITH CHLORINATED AMINO ACIDS

(75) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/515,192

(22) PCT Filed: Dec. 13, 2010

(86) PCT No.: PCT/US2010/060085
§ 371 (c)(1),
(2), (4) Date: Jul. 18, 2012

(87) PCT Pub. No.: WO2011/072288
PCT Pub. Date: Jun. 16, 2011

(65) Prior Publication Data
US 2012/0277148 A1 Nov. 1, 2012

Related U.S. Application Data

(60) Provisional application No. 61/285,955, filed on Dec. 11, 2009.

(51) Int. Cl.
*A61K 38/28* (2006.01)
*C07K 14/62* (2006.01)
*A61K 38/00* (2006.01)

(52) U.S. Cl.
CPC *C07K 14/62* (2013.01); *A61K 38/00* (2013.01)

(58) Field of Classification Search
CPC .............................. C07K 14/62; A61K 38/28
USPC ..................... 514/6.9, 5.9, 6.2, 6.3
See application file for complete search history.

(56) References Cited

U.S. PATENT DOCUMENTS

| | | | |
|---|---|---|---|
| 5,149,716 A | 9/1992 | Vertesy et al. | |
| 5,149,777 A | 9/1992 | Hansen et al. | |
| 5,491,216 A | 2/1996 | Hoffmann et al. | |
| 5,506,202 A | 4/1996 | Vertesy et al. | |
| 5,536,652 A | 7/1996 | Hennecke et al. | |
| 5,618,913 A | 4/1997 | Brange et al. | |
| 5,698,669 A | 12/1997 | Hoffmann et al. | |
| 5,700,662 A | 12/1997 | Chance et al. | |
| 5,716,927 A | 2/1998 | Balschmidt et al. | |
| 5,977,297 A | 11/1999 | Obermeier et al. | |
| 6,011,007 A | 1/2000 | Havelund et al. | |
| 6,221,633 B1 | 4/2001 | Ertl et al. | |
| 6,268,335 B1 | 7/2001 | Brader | |
| 6,465,426 B2 | 10/2002 | Brader | |
| 6,531,448 B1 | 3/2003 | Brader | |
| 6,630,348 B1 | 10/2003 | Lee et al. | |
| 7,129,211 B2 | 10/2006 | Bhattacharya et al. | |
| 7,316,999 B2 * | 1/2008 | Hoeg-Jensen et al. | 514/6.2 |
| 7,547,821 B2 | 6/2009 | Moloney et al. | |
| 2001/0036916 A1 | 11/2001 | Brader | |
| 2002/0082199 A1 | 6/2002 | Brader | |
| 2003/0104981 A1 | 6/2003 | Mandic | |
| 2003/0144181 A1 | 7/2003 | Brader | |
| 2004/0014660 A1 | 1/2004 | During et al. | |
| 2004/0053816 A1 | 3/2004 | Bhattacharya et al. | |
| 2004/0214988 A1 | 10/2004 | Tirrell et al. | |
| 2005/0014679 A1 | 1/2005 | Beals et al. | |
| 2005/0039235 A1 | 2/2005 | Moloney et al. | |
| 2005/0176621 A1 | 8/2005 | Brader et al. | |
| 2006/0217290 A1 | 9/2006 | Kohn et al. | |
| 2007/0129284 A1 | 6/2007 | Kjeldsen et al. | |
| 2007/0293426 A1 * | 12/2007 | Demuth et al. | 514/12 |
| 2008/0146492 A1 | 6/2008 | Zimmerman et al. | |
| 2008/0261872 A1 * | 10/2008 | Ghigo et al. | 514/12 |
| 2009/0048162 A1 * | 2/2009 | Ko et al. | 514/12 |
| 2009/0304814 A1 | 12/2009 | Weiss | |
| 2010/0099601 A1 | 4/2010 | Weiss | |
| 2011/0059887 A1 | 3/2011 | Weiss | |
| 2011/0077196 A1 | 3/2011 | Weiss | |
| 2011/0077197 A1 | 3/2011 | Habermann et al. | |
| 2011/0166064 A1 | 7/2011 | Weiss | |
| 2011/0195896 A1 | 8/2011 | Weiss et al. | |

FOREIGN PATENT DOCUMENTS

EP 1 090 640 A2 4/2001
WO 03053339 A2 7/2003

(Continued)

OTHER PUBLICATIONS

Beili Quan, David L. Smiley, Vasily M. Gelfanov and Richard D. DiMarchi, Site Specific Introduction of Unnatural Amino Acids at Sites Critical to Insulin Receptor Recognition and Biological Activity, Understanding Bilogy Using Peptides, American Peptide Society, 2005, pp. 311-312.

(Continued)

*Primary Examiner* — Gyan Chandra

(74) *Attorney, Agent, or Firm* — Hahn Loeser & Parks LLP

(57) ABSTRACT

An insulin analogue comprises a B-chain polypeptide incorporating a chlorinated phenylalanine. The chlorinated phenylalanine may be located at position B24. The chlorinated phenylalanine may be para-monochloro-phenylalanine. The analogue may be of a mammalian insulin, such as human insulin. A nucleic acid encodes such an insulin analogue. The chlorinated insulin analogues retain significant activity. A method of treating a patient comprises administering a physiologically effective amount of the insulin analogue or a physiologically acceptable salt thereof to a patient. Chlorine substitution-based stabilization of insulin may reduce fibrillation and thereby enhance the treatment of diabetes mellitus in regions of the developing world lacking refrigeration.

19 Claims, 13 Drawing Sheets

(56) References Cited

FOREIGN PATENT DOCUMENTS

| | | |
|---|---|---|
| WO | 2005054291 A1 | 6/2005 |
| WO | 2007081824 A2 | 7/2007 |
| WO | 2007096332 A1 | 8/2007 |
| WO | 2007081824 A3 | 2/2008 |
| WO | 2008043033 A2 | 4/2008 |
| WO | 2008043033 A3 | 11/2008 |
| WO | 2009087081 A2 | 7/2009 |
| WO | 2009129250 A2 | 10/2009 |
| WO | 2009132129 A2 | 10/2009 |
| WO | 2009132129 A3 | 1/2010 |
| WO | 2009129250 A3 | 2/2010 |
| WO | 2010014946 A2 | 2/2010 |
| WO | 2010014946 A2 | 4/2010 |
| WO | 2010014946 A3 | 4/2010 |
| WO | 2010014946 A3 | 5/2010 |
| WO | 2010063124 A1 | 6/2010 |
| WO | 2011028813 A2 | 3/2011 |
| WO | 2011072288 A2 | 6/2011 |
| WO | 2011103575 A1 | 8/2011 |

OTHER PUBLICATIONS

EP 07 84 3856 Supplementary European Search Report dated Dec. 11, 2009.
EP 09 80 3678 Supplementary European Search Report dated Jan. 30, 2012.
PCT/US2010/047546 International Search Report and Written Opinion dated May 23, 2011.
PCT/US2010/060085 International Search Report and Written Opinion dated Sep. 16, 2011.
PCT/US11/25730 International Search Report and Written Opinion dated Jul. 22, 2011.
Blanquart et al.; Characterization of IRA/IR hybrid insulin receptors using bioluminescence resonance energy transfer; Biochemical Pharmacology 76 (2008); Jul. 27, 2008, pp. 873-883.
Chen et al.; Sequences of B-Chain/Domain 1-10/1-9 of Insulin and Insulin-like Growth Factor 1 Determine Their Different Folding Behavior; Biochemistry; pp. 9225-9233; 2004.
Currie et al.; The influence of glucose-lowering therapies on cancer risk in type 2 diabetes; Diabetologia; 52(9); pp. 1766-1777; Sep. 2009.
Doig et al.; N- and C-capping preferences for all 20 amino acids in {alpha}-helical peptides; Protein Science; vol. 4; pp. 1325-1335; 1995.
Du et al.; Insulin analogs with B24 or B25 phenylalanine replaced by biphenylalanine; Acta Biochem Biophys Sin; vol. 40, No. 2; pp. 133-139; Feb. 2008.
Duckworth et al.; Degradation products of insulin generated by hepatocytes and by insulin protease; Journal of Biological Chemistry, vol. 263, No. 4, Apr. 6, 1988; pp. 1826-1833.
Garriques et al.; The effect of mutations on the structure of insulin fibrils studied by Fourier transform infrared (FTIR) spectroscopy and electron microscopy; PubMed; vol. 12; 1 page (abstract only); 2002.
Haijuan Du et al.; Insulin analogs with B24 or B25 phenylalanine replaced by bipheylalanine; ACTA Biochimica et Biophysica Sinica, vol. 40, No. 2, 2006, pp. 133-139.
Hemkens et al.; Risk of malignancies in patients with diabetes treated with human insulin or insulin analogues: a cohort study; Diabetologia 52(9); pp. 1732-1744; Sep. 2009.
Hua et al.; Design of an Active Ultrastable Single-chain Insulin Analog; The Journal of Biological Chemistry; vol. 283, No. 21; pp. 14703-14716; May 23, 2008.
Hua et al.; Mechanism of insulin fibrillation—The structure of insulin under amyloidogenic conditions resembles a protein-folding intermediate, Journal of Biological Chemistry; vol. 279, No. 20; pp. 21449-21460, XP002557730, ISSN 0021-9258; May 14, 2004.
Huang et al.; Structure-Specific Effects of Protein Topology on Cross-β Assembly: Studies of Insulin Fibrillation; Biochemistry 2006, 45, pp. 10278-10293, Aug. 24, 2006.

Kaarsholm et al.; Engineering Stability of the Insulin Monomer Fold with Application Structure-Activity Relationships; Biochemistry; 32 (40); pp. 10773-10778, Oct. 1993.
Kohn et al.; pl-shifted insulin analogs with extended in vivo time action and favorable receptor selectivity; Peptides; 28 (4); Jan. 25, 2007; pp. 935-948.
Kohn et al.; pl-shifted insulin analogs with extended in vivo time action and favorable receptor selectivity; PubMed; 28 (4); 1 page (abstract only); Jan. 25, 2007.
Kristensen et al.; Alanine Scanning Mutagenesis of Insulin; The Journal of Biological Chemistry; vol. 272, No. 20; pp. 12978-12983, May 16, 1997.
Liefvendahl et al.; Mitogenic effect of the insulin analogue glargine in malignant cells in comparison with insulin and IGF-I; PubMed; 1 page (abstract only); Apr. 7, 2008.
Liu et al.; Utilization of combined chemical modification to enhance the blood-brain barrier permeability and pharmacological activity of endomorphin-a, JPET 106, 106484, Jun. 27, 2006, pp. 1-43.
Mayer et al.; Proliferative effects of insulin analogues on mammary epithelial cells; Archives of Physiology and Biochemistry; 114(1); pp. 38-44; Feb. 2008.
Milazzo et al.; ASPB10 insulin induction of increased mitogenic responses and phenotypic changes in human breast epithelial cells; evidence for enhanced interations with the insulin-like growth factor-I receptor; PubMed; 18(1); 1 page (abstract only); Jan. 1997.
Mirmira et al.; Disposition of the phenylalanine B25 side chain during insulin-receptor and insulin-insulin interactions, Biochemistry; vol. 30, No. 33; May 1, 1991, pp. 8222-8229.
Mirmira et al.; Importance of the character and configuration of residues B24 B25 and B26 in insulin-receptor interactions, Journal of Biological Chemistry, vol. 266, No. 3; Jan. 25, 1991; pp. 1428-1436.
Mirmira et al.; Role of the Phenylalanine B24 Side Chain in Directing Insulin Interaction with Its Receptor; The Journal of Biological Chemistry; vol. 264, No. 11; pp. 6349-6354; Apr. 15, 1989.
Nakagawa, et al.; Chiral Mutagenesis of Insulin; The Journal of Biological Chemistry; vol. 281, No. 31; pp. 22386-22396; Aug. 4, 2006.
Nielsen et al.; Probing the Mechanism of Insulin Fibril Formation with Insulin Mutants; American Chemical Society; Biochemistry; vol. 40; pp. 8397-8409; Jun. 19, 2001.
Olsen et al.; The Relationship Between Insulin Bioactivity and Structure in the NH2-terminal A-chain Helix; Journal of Molecular Biology; vol. 284, Issue 2, pp. 477-488, Nov. 27, 1998.
Rajpal et al.; Single-Chain Insulins as Receptor Agonists; The Endrocrine Society; 27 pages; Feb. 19, 2009.
Shukla et al.; Analysis of signaling pathways related to cell proliferation stimulated by insulin analogs in human mammary epithelial cell lines; Endrocine-Related Cancer; 16(2); pp. 429-441; Jun. 2009.
Sleiker et al.; Modifications in the B10 and B26-30 regions of the B chain of human insulin alter affinity for the human IGF-I receptor more than for the insulin receptor; Diabetologia; 40 Suppl. 2; Jul. 1997; pp. S54-S61.
Sreekanth et al.; Structural interpretation of reduced insulin activity as seen in the crystal structure of human Arg-insulin; Biochimie; 90(3); Sep. 22, 2007; pp. 467-473.
Stemaszynska et al.; N-(2-Oxoacyl)amino Acids and Nitriles as Final Products of Dipeptide Chlorination Mediated by the Myeloperoxidase/H2O2/Cl-System, European Journal of Biochemistry, vol. 92, No. 1, Sep. 25, 1978, pp. 301-308.
Summ et al.; Binding of insulin analogs to partially purified insulin receptor from rat liver membrane (author's trans.); Hoppe Seylers Z. Physiol. Chem.; 357(5); May 1976; pp. 683-693 (Abstract only—1 page).
Tuffs; German agency suspects that insulin analogue glargine increases risk of cancer; PubMed; BMJ; 339:b2774; 1 page (no abstract available); Jul. 8, 2009.
Wan et al.; Enhancing the Activity of Insulin at the Receptor Interface: Crystal Structure and Photo-Cross-Linking of A8 Analogues; Biochemistry 2004, 43; Nov. 25, 2004; pp. 16119-16133.
Weinstein, et al.; Insulin analogues display IGF-I-like mitogenic and anti-apoptotic activities in cultured cancer cells; Diabetes/Metabolism Research and Reviews; 25(1); pp. 41-49; Jan. 2009.

(56) References Cited

OTHER PUBLICATIONS

Weiss et al.; Non-standard Insulin Design: Structure-Activity Relationships at the Periphery of the Insulin Receptor; The Journal of Molecular Biology; vol. 315; pp. 103-111, 2002.

Weiss, et al.; Activities of Monomeric Insulin Analogs at Position A8 Are Uncorrelated with Their Thermodynamic Stabilities; The Journal of Biological Chemistry; vol. 276, No. 43; pp. 40018-40024; Oct. 26, 2001.

Yang et al.; An Achilles' heel in an amyloidogenic protein and its repair: insulin fibrillation and therapeuric design; J Biol Chem. Apr. 1, 2010:285(14):10806-21, Apr. 2, 2010.

Zakova et al.; Shortened Insulin Analyogues: Marked Changes in Biological Activity Resulting from Replacement of TyrB26 and N-Methylation of Piptide Bonds in the C-Terminus of the B-Chain; Biochemistry; vol. 43; pp. 2323-2331; 2004.

Zelobowska et al.; Mitogenic potency of insulin glargine; Polish Journal of Endocrinology; vol. 60, No. 1; pp. 34-39; 2009.

Zhao et al.; Design of an insulin analog with enhanced receptor binding selectivity: rationale, structure, and therapeutic implications; J. Biol. Chem. 284(46); Sep. 22, 2009; pp. 32178-32187.

Liu Hong-Mei, Liu Xue-Feng, Yao Jin-Long, Wang Chang-Lin, Yu Ye, and Wang Rui; Utilization of Combined Chemical Modifications to Enhance the Blood-Brain Barrier Permeability and Pharmacological Activity of Endomorphin-1; The Journal of Pharmacology and Experimental Therapeutics, vol. 319. No. 1; Jun. 26, 2006.

Emma M. Bingham, David Hopkins, Diarmuid Smith, Andrew Pernet, William Hallett, Laurence Reed, Paul K. Marsden, and Stephanie A. Amiel; "The Role of Insulin in Human Brian Glucose Metabolism an Fluoro-Deoxyglucose Positron Emission Tomography Study"; Diabetes, vol. 51, Dec. 2002.

Beili Quan, David L Smiley, Vasily M. Gelfanov and Richard D. DiMarchi; Site Specific Introduction of Unnatural Amino Acids at Sites Critical to Insulin Receptor Recognition and Biological Activity; American Peptide Society, 2005.

Klaus Mailer et al., "Flourine in Pharmaceuticals: Looking Beyond Intuition", Science vol. 317, pp. 1881-1886, Sep. 28, 2007.

Jack D. Dunitz and Robin Talyer; "Organic Fluorine Hardly Ever Accepts Hydrogen Bonds", VCH Verlagsgesellschaft mbH, D-69451 Weinheim, 1997.

Peter Politzer, Pat Lane, Monica C. Concha, Yuguang Ma, Jane S. Murray, "An overview of Halogen Bonding", Springer-Verlag 2006.

Hardegger, L.A., Kuhn, B., Spinnler, B., Anselm, L., Ecabert, R., Stihle, M., Gsel, B., Thoma, R., Diez, J., Benz, J., Plancher, J, -M., Hartmann, G., Banner, D.W., Haap, W. and Diederich, F. (2011), Systematic Investigation of Halogen Bonding in Protein-Ligand Interactions. Angew. Chem. Int. Ed., 50: 314-318. doi: 10.1002/anie.201006781.

Poonam Shah & Andrew D. Westwell, "The role of flourine in medicinal chemistry", Journal of Enzyme Inhibition and Medicinal Chemistry, Oct. 2007; 22(5): 527-540.

Andrew V. Razgulin and Sandro Mecozzi, "Binding Properties of Aromatic Carbon-Bound Fluorine", J. Med. Chem. 2006, 49, 7902-7906.

Peng Zhou, Jianwei Zou, Feifei Tian, and Zhicai Shang, "Fluorine Bonding—How Does It Work in Protein-Ligand Interactions?", J. Chem. Inf. Model, 2009, 49, 2344-2355.

J. Samanen, T. Cash, D. Narindray, E. Brandeis, T. Yellin, and D. Regoli, "The Role of Position 4 in Angiotensin II Antagonism: A Structure-Activity Study", J. Med. chem. 1989, 32, 1366-1370.

Deborah L. Heyl and Henry I. Mosberg, "Substution on the Phe3 Aromatic Ring in Cyclic . . . ", J. Med. Chem. 1992, 35, 1535-1541.

Sophie PUrser, Peter R. Moore, Steve Swallow and Véronique Gouverneur, "Fluroine in medicinal Chemistry", Chemical Society Reviews, www.rsc.org/chemsocrev, vol. 37, No. 2, Feb. 2008, pp. 237-432.

Kashif Hanif, Kshitji Gupta, Suparna Gupta, Y.K. Gupta, Souvik Maiti, Santosh Pasha, Chmeric peptide of met-enkephalin and FMRFa: Effect of chlorination on conformation and analgesia, Neuro Science Letters 403 (2006) 131-135.

Daniel Levy, "The Selective Chloromerucration of Insulin", Biochimica et Biophysica Acta, 317 (1973) 473-481.

Adnan Memic and Mark R. Spaller, How Do Halogen Substituents Contribute to Protein-Binding Interactions? A Thermodynamic Study of Peptide Lignads with Diverse Aryl Halides, ChemBioChem 2008, 9 2793-2795.

David I. Pattison, Clare L. Hawkins, and Michael J. Davies, Hypochlorous Acid-mediated Protein Oxidation: How Imporant Are Chloramine Transfer Reactions and Protein Tertiary Structure?.

PCT/US2010/060085 Extended Search Report, Jul. 18, 2013.

PCT/US2010/060085 International Search Report and Written Opinion, Aug. 6, 2013.

* cited by examiner

PROINSULIN

MODEL

INSULIN ANALOGUES WITH CHLORINATED AMINO ACIDS

CROSS REFERENCE TO RELATED APPLICATIONS

This application is a national stage application of PCT/US2010/060085 which was filed on Dec. 13, 2010, which is a non-provisional of U.S. Patent Application No. 61/285,955 which was filed on Dec. 11, 2009.

STATEMENT REGARDING FEDERALLY SPONSORED RESEARCH OR DEVELOPMENT

This invention was made with government support under cooperative agreements awarded by the National Institutes of Health under grant numbers DK40949 and DK074176. The U.S. government may have certain rights to the invention.

TECHNICAL FIELD

This invention relates to polypeptides that are resistant to thermal degradation. More particularly, this invention relates to thermally stabilized insulin analogues. Even more particularly, this invention relates to insulin analogues that are chemically and thermally stabilized by the incorporation of the element chlorine into an amino acid of the insulin analogue. Chlorine is classified as a halogen and is distinguished from the ordinary constituents of proteins by its atomic radius, electronegativity, stereoelectronic distribution of partial charges, and transmitted effects on the stereoelectronic properties of neighboring atoms in a molecule.

BACKGROUND OF THE INVENTION

The engineering of ultra-stable proteins, including therapeutic agents and vaccines, may have broad societal benefits in regions of the developing world where electricity and refrigeration are not consistently available. An example of a therapeutic protein susceptible to thermal degradation is provided by insulin. The challenge posed by its chemical and physical degradation is deepened by the pending epidemic of diabetes mellitus in Africa and Asia. Because chemical degradation rates of insulin analogues correlate inversely with their relative stabilities, the design of ultra-stable formulations may enhance the safety and efficacy of insulin replacement therapy in such challenged regions.

The utility of some halogen substitutions in small organic molecules is known in medicinal chemistry. Fluorinated functional groups are critical to the efficacy of such widely prescribed small molecules as atorvastatin (Liptor™), an inhibitor of cholesterol biosynthesis, and fluoxetine hydrochloride (Prozac™), a selective serotonin reuptake inhibitor used in the treatment of depression and other affective disorders. Although the atomic radius of fluorine is similar to that of hydrogen, its large inductive effects modify the stereoelectronic properties of these drugs, in turn enhancing their biological activities. Similar considerations of physical organic chemistry pertain to the incorporation of larger halogen atoms, such as chlorine. The small molecule montelukast sodium (Singulair™) is a leukotriene inhibitor whose pharmaceutical properties are enhanced by covalent incorporation of a chlorine atom. Additionally, the use of fluorine-substituted amino acids in an insulin analogue is provided in International Patent Application No. PCT/US2009/52477 filed 31 Jul. 2009.

Modulation of the chemical, physical, and biological properties of proteins by the site-specific incorporation of chlorine atoms into modified amino acids are less well characterized in the scientific literature than are the above effects of incorporation of fluorine atoms.

Aromatic side chains may engage in a variety of weakly polar interactions, involving not only neighboring aromatic rings but also other sources of positive- or negative- electrostatic potential. Examples include main-chain carbonyl- and amide groups in peptide bonds.

Administration of insulin has long been established as a treatment for diabetes mellitus. Insulin is a small globular protein that plays a central role in metabolism in vertebrates. Insulin contains two chains, an A chain, containing 21 residues and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). Although the structure of proinsulin has not been determined, a variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM).

Extensive X-ray crystallographic studies have been undertaken of $Zn^{2+}$-coordinated insulin hexamers, the physiological storage form. Multiple crystal forms have been described in vitro, defining three structural families, designated $T_6$, $T_3R^f_3$ and $R_6$. In these hexamers two Zn ions are believed to lie along the central axis of the hexamer, each coordinated by three histidines (HisB10); additional low-affinity Zn-binding sites have been observed in some crystal forms. The T-state protomer resembles the structure of an insulin monomer in solution. The R-state protomer exhibits a change in the secondary structure of the B-chain: the central α-helix extends to B1 (the R state) or to B3 (frayed $R^f$ state).

Insulin functions in the bloodstream as a monomer, and yet it is the monomer that is believed to be most susceptible to fibrillation and most forms of chemical degradation. The structure of an insulin monomer, characterized in solution by NMR, is shown in FIG. 1D. The A-chain consists of an N-terminal α-helix (residues A1-A8), non-canonical turn (A9-A12), second α-helix (A12-A18), and C-terminal extension (A19-A21). The B chain contains an N-terminal arm (B1-B6), O-turn (B7-B10), central α-helix (B9-B19), β-turn (B20-B23), β-strand (B24-B28), and flexible C-terminal residues B29-B30. The two chains pack to form a compact globular domain stabilized by three disulfide bridges (cystines A6-A11, A7-B7, and A20-B19).

Absorption of regular insulin is limited by the kinetic lifetime of the Zn-insulin hexamer, whose disassembly to smaller dimers and monomers is required to enable transit through the endothelial lining of capillaries. The essential idea underlying the design of Humalog® and Novolog® is to accelerate disassembly. This is accomplished by destabilization of the classical dimer-forming surface (the C-terminal anti-parallel β-sheet). Humalog® contains substitutions ProB28→Lys and LysB29→Pro, an inversion that mimics the sequence of IGF-I. Novolog® contains the substitution ProB28→Asp. Although the substitutions impair dimerization, the analogs are competent for assembly of a phenol- or meta-cresol-stabilized zinc hexamer. This assembly protects the analog from fibrillation in the vial, but following subcutaneous injection, the hexamer rapidly dissociates as the phenol (or m-cresol) and zinc ions diffuse away. The instability of these analogs underlies their reduced shelf life on dilution by the patient or health-care provider. It would be useful for an insulin analogue to augment the intrinsic stability of the insulin monomer while retaining the variant dimer-related β-sheet of Humalog®.

Use of zinc insulin hexamers during storage is known and represents a classical strategy to retard physical degradation and chemical degradation of a formulation in the vial or in the reservoir of a pump. Because the zinc insulin hexamer is too large for immediate passage into capillaries, the rate of absorption of insulin after subcutaneous injection is limited by the time required for dissociation of hexamers into smaller dimers and monomer units. Therefore, it would advantageous for an insulin analogue to be both (a) competent to permit hexamer assembly at high protein concentration (as in a vial or pump) and yet (b) sufficiently destabilized at the dimer interface to exhibit accelerated disassembly—hence predicting ultra-rapid absorption from the subcutaneous depot. These structural goals walk a fine line between stability (during storage) and instability (following injection).

Amino-acid substitutions in insulin have been investigated for effects on thermodynamic stability and biological activity. No consistent relationship has been observed between stability and activity. Whereas some substitutions that enhance thermodynamic stability also enhance binding to the insulin receptor, other substitutions that enhance stability impede such binding. The effects of substitution of $Thr^{A8}$ by several other amino acids has been investigated in wild-type human insulin and in the context of an engineered insulin monomer containing three unrelated substitutions in the B-chain ($His^{B10}$→Asp, $Pro^{B28}$→Lys, and $Lys^{B29}$→Pro) have been reported. Examples are also known in the art of substitutions that accelerate or delay the time course of absorption. Such substitutions (such as $Asp^{B28}$ in Novalog® and [$Lys^{B28}$, $Pro^{B29}$] in Humalog®) can be and often are associated with more rapid fibrillation and poorer physical stability. Indeed, in one study a series of ten analogues of human insulin was tested for susceptibility to fibrillation, including $Asp^{B28}$-insulin and $Asp^{B10}$-insulin. All ten were found to be more susceptible to fibrillation at pH 7.4 and 37° C. than is human insulin. The ten substitutions were located at diverse sites in the insulin molecule and are likely to be associated with a wide variation of changes in classical thermodynamic stability. Although a range of effects has been observed, no correlation exists between activity and thermodynamic stability.

Insulin is a small globular protein that is highly amenable to chemical synthesis and semi-synthesis, which facilitates the incorporation of nonstandard side chains. Insulin contains three phenylalanine residues (positions B1, B24, and B25) and a structurally similar tyrosine at position B26. Conserved among vertebrate insulins and insulin-like growth factors, the aromatic ring of $Phe^{B24}$ packs against (but not within) the hydrophobic core to stabilize the super-secondary structure of the B-chain. $Phe^{B24}$ lies at the classical receptor-binding surface and has been proposed to direct a change in conformation on receptor binding. $Phe^{B25}$ projects from the surface of the insulin monomer whereas $Tyr^{B26}$ packs near aliphatic side chains ($Ile^{A2}$, $Val^{A3}$, and $Val^{B12}$) at one edge of the core. The B24-related conformational change is proposed to enable $Phe^{B25}$ and $Tyr^{B26}$ to contact distinct domains of the insulin receptor.

The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the insulin molecule to increase or decrease the risk of fibrillation is highly unpredictable.

Fibrillation, which is a serious concern in the manufacture, storage and use of insulin and insulin analogues for diabetes treatment, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, diabetic individuals optimally must keep insulin refrigerated prior to use. Fibrillation of insulin or an insulin analogue can be a particular concern for diabetic patients utilizing an external insulin pump, in which small amounts of insulin or insulin analogue are injected into the patient's body at regular intervals. In such a usage, the insulin or insulin analogue is not kept refrigerated within the pump apparatus and fibrillation of insulin can result in blockage of the catheter used to inject insulin or insulin analogue into the body, potentially resulting in unpredictable blood glucose level fluctuations or even dangerous hyperglycemia. At least one recent report has indicated that lispro insulin (an analogue in which residues B28 and B29 are interchanged relative to their positions in wild-type human insulin; trade name Humalog®) may be particularly susceptible to fibrillation and resulting obstruction of insulin pump catheters.

Insulin fibrillation is an even greater concern in implantable insulin pumps, where the insulin would be contained within the implant for 1-3 months at high concentration and at physiological temperature (i.e., 37° C.), rather than at ambient temperature as with an external pump. Additionally, the agitation caused by normal movement would also tend to accelerate fibrillation of insulin. In spite of the increased potential for insulin fibrillation, implantable insulin pumps are still the subject of research efforts, due to the potential advantages of such systems. These advantages include intraperitoneal delivery of insulin to the portal circulatory system, which mimics normal physiological delivery of insulin more closely than subcutaneous injection, which provides insulin to the patient via the systemic circulatory system. Intraperitoneal delivery provides more rapid and consistent absorption of insulin compared to subcutaneous injection, which can provide variable absorption and degradation from one injection site to another. Administration of insulin via an implantable pump also potentially provides increased patient convenience. Whereas efforts to prevent fibrillation, such as by addition of a surfactant to the reservoir, have provided some improvement, these improvements have heretofore been considered insufficient to allow reliable usage of an implanted insulin pump in diabetic patients outside of strictly monitored clinical trials.

As noted above, the developing world faces a challenge regarding the safe storage, delivery, and use of drugs and vaccines. This challenge complicates the use of temperature-sensitive insulin formulations in regions of Africa and Asia lacking consistent access to electricity and refrigeration, a challenge likely to be deepened by the pending epidemic of diabetes in the developing world. Insulin exhibits an increase in degradation rate of 10-fold or more for each 10° C. increment in temperature above 25° C., and guidelines call for storage at temperatures <30° C. and preferably with refrigeration. At higher temperatures insulin undergoes both chemical degradation (changes in covalent structure such as formation of iso-aspartic acid, rearrangement of disulfide bridges, and formation of covalent polymers) and physical degradation (non-native aggregation and fibrillation).

Amino-acid substitutions have been described in insulin that stabilize the protein but augment its binding to the insulin receptor (IR) and its cross-binding to the homologous receptor for insulin-like growth factors (IGFR) in such a way as to confer a risk of carcinogenesis. An example known in the art is provided by the substitution of $His^{B10}$ by aspartic acid. Although $Asp^{B10}$-insulin exhibits favorable pharmaceutical properties with respect to stability and pharmacokinetics, its enhanced receptor-binding properties were associated with tumorigenesis in Sprague-Dawley rats. Although there are many potential substitutions in the A- or B chains that can be introduced into $Asp^{B10}$-insulin or related analogues to reduce its binding to IR and IGFR to levels similar to that of human insulin, such substitutions generally impair the stability of insulin (or insulin analogues) and increase its susceptibility to chemical and physical degradation. It would be desirable to discover a method of modification of insulin and of insulin analogues that enabled "tuning" of receptor-binding affinities while at the same time enhancing stability and resistance to fibrillation. Such applications would require a set of stabilizing modifications that reduce binding to IR and IGFR to varying extent so as to offset the potential carcinogenicity of analogues that are super-active in their receptor-binding properties.

Therefore, there is a need for alternative insulin analogues, including those that are stable during storage but are simultaneously fast-acting.

SUMMARY OF THE INVENTION

It is, therefore, an aspect of the present invention to provide an insulin analogue that provides altered properties, such as improved stability, by chlorine substitution in an amino acid, where the analogue also maintains at least a portion of biological activity of the corresponding non-chlorinated insulin or insulin analogue.

In addition or in the alternative, it is an aspect of the present invention to provide an insulin analogue that is a fast acting insulin but also has improved stability over previous fast-acting insulin analogues.

In general, the present invention provides an insulin analogue comprising a B-chain polypeptide which incorporates a chlorinated amino acid. In one embodiment, the chlorinated amino acid is phenylalanine at position B24. In one particular embodiment, the chlorinated phenylalanine is para-monochloro-phenylalanine. In addition or in the alternative, the insulin analogue may be a mammalian insulin analogue, such as an analogue of human insulin. In one particular set of embodiments, the B-chain polypeptide comprises an amino acid sequence selected from the group consisting of SEQ ID NOS: 4-8 and polypeptides having three or fewer additional amino acid substitutions thereof.

Also provided is a nucleic acid encoding an insulin analogue comprising a B-chain polypeptide that incorporates a chlorinated phenylalanine at position B24 such as para-monochloro-phenylalanine. In one example, the chlorinated phenylalanine is encoded by a stop codon, such as the nucleic acid sequence TAG. An expression vector may comprise such a nucleic acid and a host cell may contain such an expression vector.

The invention also provides a method of treating a patient. The method comprises administering a physiologically effective amount of an insulin analogue or a physiologically acceptable salt thereof to the patient, wherein the insulin analogue or a physiologically acceptable salt thereof contains a chlorinated amino acid. In one embodiment, an insulin B-chain incorporates a chlorinated phenylalanine at position B24. In one particular embodiment, the chlorinated phenylalanine is para-monochloro-phenylalanine. In addition or in the alternative, the insulin analogue may a mammalian insulin analogue, such as an analogue of human insulin. Furthermore, the B-chain polypeptide may comprise an amino acid sequence selected from the group consisting of SEQ ID NOS: 4-8 and polypeptides having three or fewer additional amino-acid substitutions thereof.

DESCRIPTION OF EMBODIMENTS

The present invention is directed an insulin analogue that provides greater stability by chlorine substitution in an amino acid, where the analogue then maintains at least a portion of biological activity of the corresponding non-chlorinated insulin or insulin analogue. Particularly, the present invention provides insulin analogues that provide greater stability by substitution of chlorine in an amino acid, where the analogue then maintains at least a portion of biological activity of the corresponding non-chlorinated insulin or insulin analogue. In one particular embodiment, the present invention provides insulin analogues that contain a para-monochloro-phenylalanine (4Cl-Phe$^{B24}$) residue as a substitution for wild type phenylalanine at position B24.

The present invention is not limited, however, to human insulin and its analogues. It is also envisioned that these substitutions may also be made in animal insulins such as porcine, bovine, equine, and canine insulins, by way of non-limiting examples.

Furthermore, in view of the similarity between human and animal insulins, and use in the past of animal insulins in human diabetic patients, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. In one example, the insulin analogue of the present invention contains three or fewer conservative substitutions other than the 4Cl-Phe$^{B24}$ substitution of the present invention. In another example, the insulin analogue of the present invention contains one or fewer conservative substitutions other than the 4Cl-Phe$^{B24}$ substitution of the present invention.

Figure 2A:
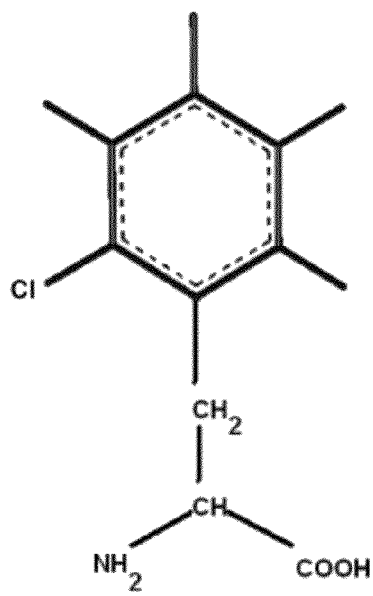
FIG. 2A is a representation of ortho-monochlorinated-phenylalanine (2Cl -Phe).
Figure 2B:
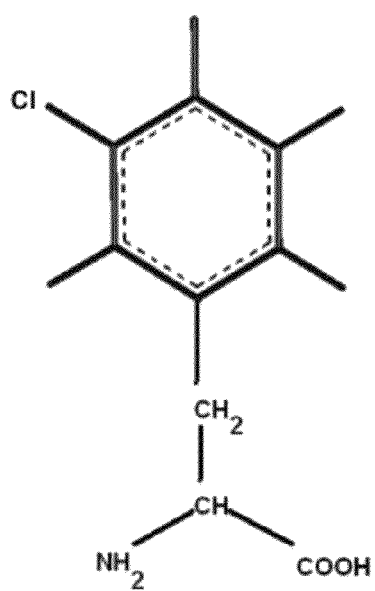
FIG. 2B is a representation of meta-monochlorinated-phenylalanine (3Cl-Phe).
Figure 2C:
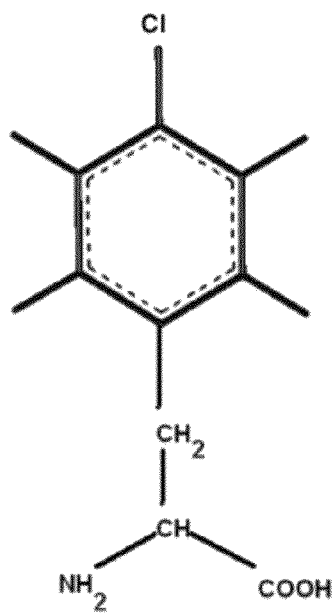
FIG. 2C is a representation of para-monochlorinated-phenylalanine (4Cl-Phe).

As used in this specification and the claims, various amino acids in insulin or an insulin analogue may be noted by the amino acid residue in question, followed by the position of the amino acid, optionally in superscript. The position of the amino acid in question includes the A or B chain of insulin where the substitution is located. Thus, Phe$^{B24}$ denotes a phenylalanine at the twenty fourth amino acid of the B chain of insulin, while Phe$^{B25}$ denotes a phenylalanine at the twenty fifth amino acid of the B chain of insulin. A chlorinated amino acid may be indicated with the prefix "Cl-." Therefore, chlorinated phenylalanine may be abbreviated "Cl-Phe." In the case of phenylalanine, the position of the chlorine substituents or substituents on the phenyl side chain may be further indicated by the number of the carbon to which the chlorine is attached. Therefore, ortho-monochloro-phenylalanine (shown in FIG. 2B) is abbreviated "2Cl-Phe," meta-monochloro-phenylalanine (shown in FIG. 2C) is abbreviated "3Cl-Phe" and para-monochloro-phenylalanine (shown in FIG. 2D) is abbreviated 4Cl-Phe.

Figure 1A:
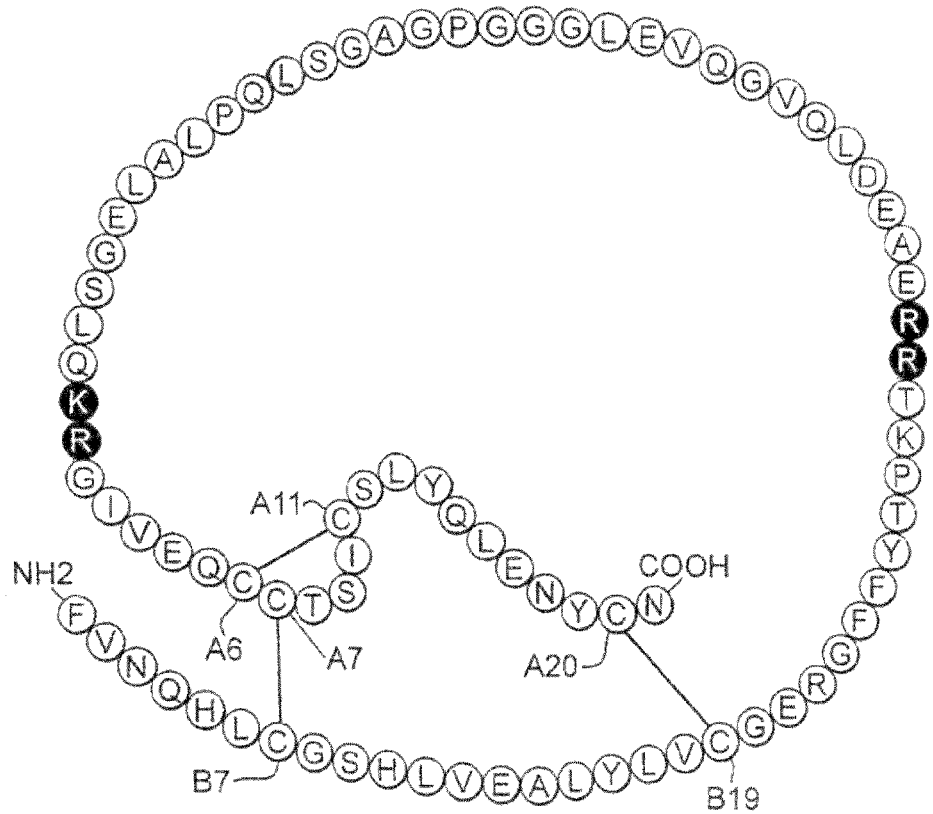
FIG. 1A is a schematic representation of the sequence of human proinsulin including the A- and B-chains and the connecting region shown with flanking dibasic cleavage sites (filled circles) and C-peptide (open circles).
Figure 1B:
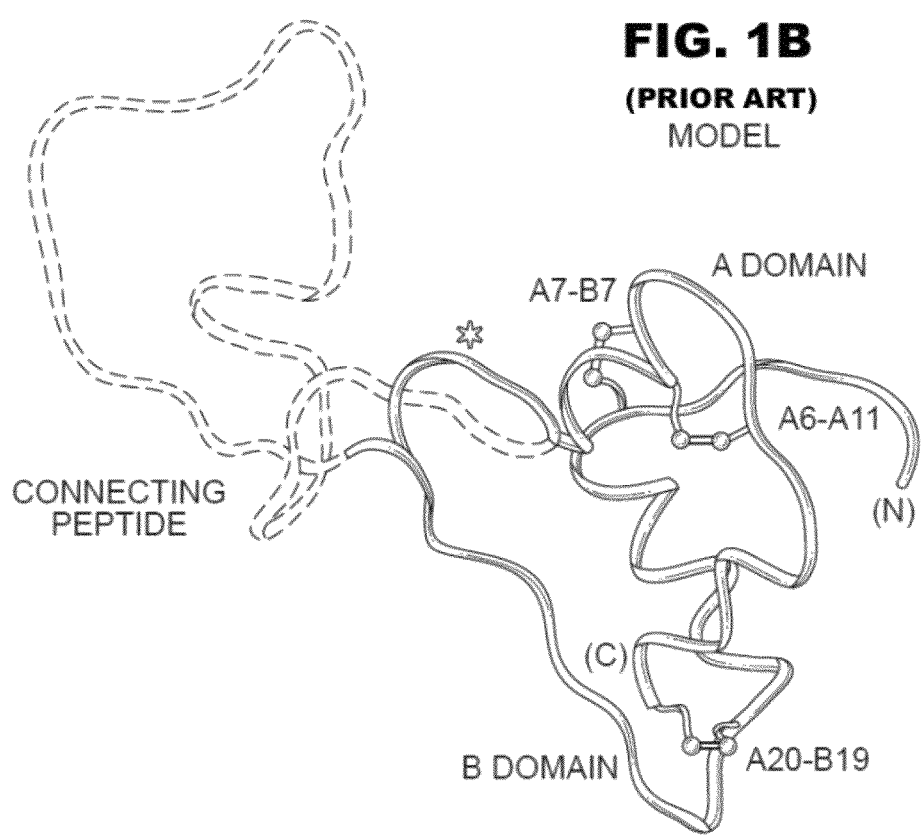
FIG. 1B is a structural model of proinsulin, consisting of an insulin-like moiety and a disordered connecting peptide (dashed line).
Figure 1C:
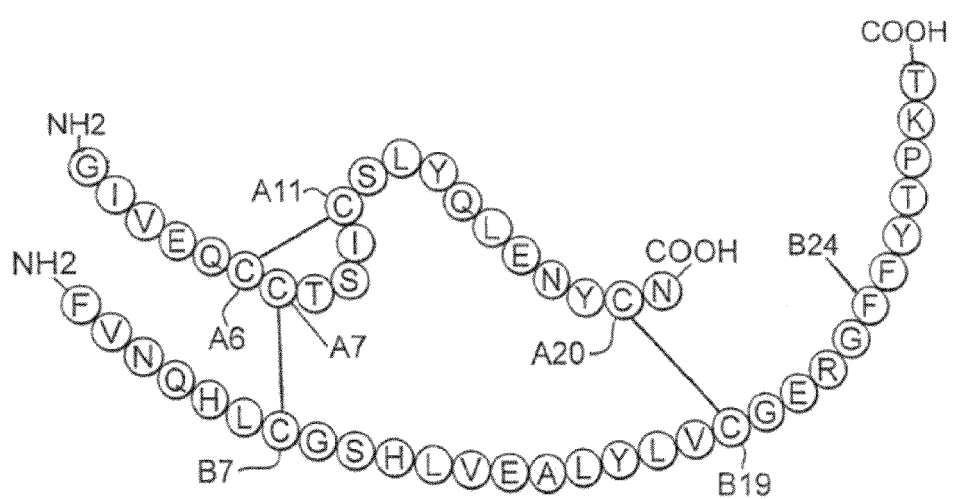
FIG. 1C is a schematic representation of the sequence of human insulin indicating the position of residue B24 in the B-chain.
Figure 1D:
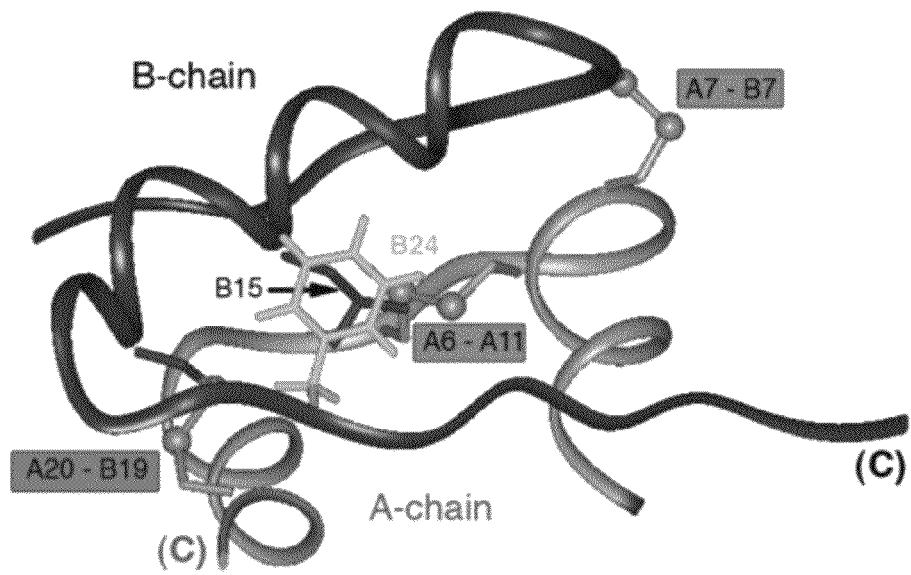
FIG. 1D is a ribbon model of an insulin monomer showing aromatic residue of $Phe^{B24}$ in relation to the three disulfide bridges. The adjoining side chains of $Leu^{B15}$ (in black) and $Phe^{B24}$ (in gray) are shown. The A- and B-chain chains are shown, and the disulfide bridges as balls and sticks.
Figure 1E:
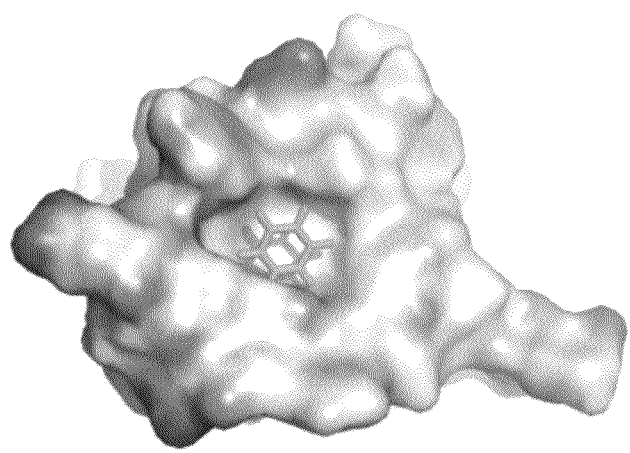
FIG. 1E is a space-filling model of insulin showing the $Phe^{B24}$ side chain within a pocket at the edge of the hydrophobic core.

The phenylalanine at B24 is an invariant amino acid in functional insulin and contains an aromatic side chain. The biological importance of Phe$^{B24}$ in insulin is indicated by a clinical mutation (Ser$^{B24}$) causing human diabetes mellitus. As illustrated in FIGS. 1D and 1E, and while not wishing to be bound by theory, Phe$^{B24}$ is believed to pack at the edge of a hydrophobic core at the classical receptor binding surface. The models are based on a crystallographic protomer (2-Zn molecule 1; Protein Databank identifier 4INS). Lying within the C-terminal β-strand of the B-chain (residues B24-B28), Phe$^{B24}$ adjoins the central α-helix (residues B9-B19). One face and edge of the aromatic ring sit within a shallow pocket defined by Leu$^{B15}$ and Cys$^{B19}$; the other face and edge are exposed to solvent (FIG. 1E). This pocket is in part surrounded by main-chain carbonyl and amide groups and so creates a complex and asymmetric electrostatic environment.

It is envisioned that the substitutions of the present invention may be made in any of a number of existing insulin analogues. For example, the chlorinated Phe$^{B24}$ substitution provided herein may be made in insulin analogues such as Lispro (KP) insulin, insulin Aspart, other modified insulins or insulin analogues, or within various pharmaceutical formulations, such as regular insulin, NPH insulin, lente insulin or ultralente insulin, in addition to human insulin. Aspart insulin contains an Asp$^{B28}$ substitution and is sold as Novalog such as DKP insulin, described more fully below, or miniproinsulin, a proinsulin analogue containing a dipeptide (Ala-Lys) linker between the A chain and B chain portions of insulin in place of the normal 35 amino acid connecting region between the C-terminal residue of the B chain and the N-terminal residue of the A chain (See FIG. 1B). Incorporation of chlorinated-Phe at position B24 in DKP-insulin (or other insulin analogues that contain Asp$^{B10}$ or that exhibit receptor-binding affinities higher than that of human insulin) can reduce their receptor-binding affinities to be similar to or below that of human insulin and so potentially enable clinical use. In this manner the cross-binding of insulin analogues to the mitogenic IGFR may also be reduced.

The amino-acid sequence of human proinsulin is provided, for comparative purposes, as SEQ ID NO: 1.

```
(proinsulin)
                                                                        SEQ ID NO: 1
Phe-Val-Asn-Gln-His-Leu-Cys-Gly-Ser-His-Leu-Val-Glu-Ala-Leu-Tyr-Leu-Val-Cys- Gly-Glu-Arg-Gly-Phe-Phe-Tyr-Thr-Pro-Lys-Thr-Arg-Arg-Glu-Ala-Glu-Asp-Leu-Gln- Val-Gly-Gln-Val-Glu-Leu-Gly-Gly-Gly-Pro-Gly-Ala-Gly-Ser-Leu-Gln-Pro-Leu-Ala- Leu-Glu-Gly-Ser-Leu-Gln-Lys-Arg-Gly-Ile-Val-Glu-Gln-Cys-Cys-Thr-Ser-Ile-Cys- Ser-Leu-Tyr-Gln-Leu-Glu-Asn-Tyr-Cys-Asn
```

The amino acid sequence of the A chain of human insulin is provided as SEQ ID NO: 2.

```
(A chain)
                                                                        SEQ ID NO: 2
Gly-Ile-Val-Glu-Gln-Cys-Cys-Thr-Ser-Ile-Cys-Ser-Leu-Tyr-Gln-Leu-Glu-Asn-Tyr- Cys-Asn
``` whereas Lispro insulin contains Lys$^{B28}$ and Pro$^{B29}$ substitutions and is known as and sold under the name Humalog®.

The amino acid sequence of the B chain of human insulin is provided as SEQ ID NO: 3.

```
(B chain)
                                                                        SEQ ID NO: 3
Phe-Val-Asn-Gln-His-Leu-Cys-Gly-Ser-His-Leu-Val-Glu-Ala-Leu-Tyr-Leu-Val-Cys- Gly-Glu-Arg-Gly-Phe-Phe-Tyr-Thr-Pro-Lys-Thr
```

These analogues are described in U.S. Pat. Nos. 5,149,777 and 5,474,978. Both of these analogues are known as fast-acting insulins.

While not wishing to be bound by theory, the chloro substitution at the para position of an aromatic ring is believed to be buried within the dimer interface (4Cl-Phe$^{B24}$) and is also believed to accelerate hexamer disassembly by creating an unfavorable alignment of chloro-aromatic electrostatic dipole moments, pairwise juxtaposed at each dimer interface within the hexamer. This is believed to permit the insulin analogue to be formulated in the presence of Zn$^{2+}$ ions and still retain the ability to be a fast-acting (meal time) insulin analogue.

A chlorinated-Phe substitution, including one at B24, may also be introduced into analogues of human insulin that, while not previously clinically used, are still useful experimentally, Further combinations of other substitutions are also within the scope of the present invention. It is also envisioned that the substitutions of the present invention may also be combined with substitutions of prior known insulin analogues. For example, the amino acid sequence of an analogue of the B chain of human insulin containing the Lys$^{B28}$ Pro$^{B29}$ substitutions of lispro insulin (Humalog®), in which the chlorinated Phe substitution may also be introduced, is provided as SEQ ID NO: 4. Likewise, the amino acid sequence of an analogue of the B chain of human insulin containing the Asp$^{B28}$ substitution of aspart insulin, in which a chlorinated-Phe$^{B24}$ substitution may also be introduced, is provided as SEQ ID NO: 5.

SEQ ID NO: 4
Phe-Val-Asn-Gln-His-Leu-Cys-Gly-Ser-His-Leu-Val-Glu-Ala-Leu-Tyr-Leu-Val-Cys-

Gly-Glu-Arg-Gly-Phe-Phe-Tyr-Thr-Lys-Pro-Thr

SEQ ID NO: 5
Phe-Val-Asn-Gln-His-Leu-Cys-Gly-Ser-His-Leu-Val-Glu-Ala-Leu-Tyr-Leu-Val-Cys-

Gly-Glu-Arg-Gly-Phe-Phe-Tyr-Thr-Asp-Lys-Thr

A chlorinated-Phe$^{B24}$ substitution may also be introduced in combination with other insulin analogue substitutions such as analogues of human insulin containing His substitutions at residues A4, A8 and/or B1 as described more fully in co-pending International Application No. PCT/US07/00320 and U.S. application Ser. No. 12/160,187, the disclosures of which are incorporated by reference herein. For example, a 4Cl-Phe$^{B24}$ substitution may be present with [His$^{A4}$, His$^{A8}$], and/or His$^{B1}$ substitutions in an insulin analogue or proinsulin analogue having the amino acid sequence represented by SEQ ID NO: 6, activity, designated DKP-insulin, which contains the substitutions Asp$^{B10}$ (D), Lys$^{B28}$ (K) and Pro$^{B29}$ (P). These three substitutions on the surface of the B-chain are believed to impede formation of dimers and hexamers. Use of an engineered monomer circumvents confounding effects of self-assembly on stability assays. The structure of DKP-insulin closely resembles a crystallographic protomer. The sequence of the B-chain polypeptide for DKP insulin is provided as SEQ ID NO: 8.

SEQ ID NO: 6
R1-Val-Asn-Gln-His-Leu-Cys-Gly-Ser-His-Leu-Val-Glu-Ala-Leu-Tyr-

Leu-Val-Cys-Gly-Glu-Arg-Gly-Phe-Phe-R2-Thr-R3-R4-Thr-Xaa$_{0-35}$-

Gly-Ile-Val-R5-Gln-Cys-Cys-R6-Ser-Ile-Cys-Ser-Leu-Tyr-Gln-Leu-Glu-

Asn-Tyr-Cys-Asn;

wherein R1 is His or Phe; wherein R2 is Tyr or Phe, R3 is Pro, Lys, or Asp; wherein R4 is Lys or Pro; wherein R5 is His or Glu; wherein R6 is His or Thr; and wherein Xaa$_{0-35}$ is 0-35 of any amino acid or a break in the amino acid chain;

(DKP B-Chain Sequence)
SEQ ID NO: 8
Phe-Val-Asn-Gln-His-Leu-Cys-Gly-Ser-Asp-Leu-Val-Glu-Ala-Leu-Tyr-Leu-Val-Cys- Gly-Glu-Arg-Gly-Phe-Phe-Tyr-Thr-Lys-Pro-Thr and further wherein at least one substitution selected from the group of the following amino acid substitutions is present:
R1 is His; and
R6 is His; and
R5 and R6 together are His.

The 4Cl-Phe$^{B24}$ substitution may also be introduced into a single chain insulin analogue as disclosed in co-pending U.S. patent application Ser. No. 12/419,169, the disclosure of which is incorporated by reference herein.

It is also envisioned that the chlorinated-Phe$^{B24}$ substitution may be introduced into an insulin analogue containing substitutions in the insulin A-chain. For example, an insulin analogue may additionally contain a lysine, histidine or arginine substitution at position A8, as shown in SEQ ID NO: 7, instead of the wild type threonine at position A8 (see SEQ ID NO: 2).

Analogues of KP-insulin may be prepared by trypsin-catalyzed semi-synthesis and purified by high-performance liquid chromatography (Mirmira, R. G., and Tager, H. S., 1989. J. Biol. Chem. 264: 6349-6354.) This protocol employs (i) a synthetic octapeptide representing residues (N)-GF*FYT KPT (including modified residue (F*) and "KP" substitutions (underlined); SEQ ID NO: 9) and (ii) truncated analogue des-octapeptide[B23-B30]-insulin (DOI; SEQ ID NO: 15). Because the octapeptide differs from the wild-type B23-B30 sequence (GFFYTPKT; SEQ ID NO: 10) by interchange of Pro$^{B28}$ and Lys$^{B29}$ (italics), protection of the lysine ε-amino group is not required during trypsin treatment. In brief under this protocol, des-octapeptide insulin (150 mg) and octapeptide (150 mg) is dissolved in a mixture of dimethylacetamide/

SEQ ID NO: 7
Gly-Ile-Val-Glu-Gln-Cys-Cys-Xaa-Ser-Ile-Cys-Ser-Leu-Tyr-Gln-Leu-Glu-Asn-Tyr-

Cys-Asn
[Xaa = His, Arg, or Lys]

As mentioned above, the 4Cl-Phe$^{B24}$ substitution may be introduced within an engineered insulin monomer of high 1,4-butandiol/0.2 M Tris acetate (pH 8) containing 10 mM calcium acetate and 1 mM ethylene diamine tetra-acetic acid (EDTA) (35:35:30, v/v, 4 mL). The 5-fold molar excess of octapeptide over DOI ensures that the reverse reaction of trypsin (proteolytic direction) is prevented by substrate saturation. The final pH is adjusted to 7.0 with 0.1 mL of N-methylmorpholine. The solution is cooled to 12° C., and 1.5 mg of trypsin is added and incubated for 2 days at 12° C. An additional 1.5 mg of trypsin is added after 24 hr. The reaction is acidified with 0.1% trifluoroacetic acid and purified by preparative reverse-phase HPLC (C4). The product may then be verified by mass spectrometry using matrix-assisted laser desorption/ionization time-of-flight (MALDI-TOF; Applied Biosystems, Foster City, Calif.). The general protocol for solid-phase synthesis is as described (Merrifield et al., 1982. *Biochemistry* 21: 5020-5031). 9-fluoren-9-yl-methoxy-carbonyl (F-moc)-protected phenylalanine analogues are available from Chem-Impex International (Wood Dale, Ill.).

Circular dichroism (CD) spectra may be obtained at 4° C. and 25° C. using an Aviv spectropolarimeter (Weiss et al., *Biochemistry* 39: 15429-15440). Samples may contain ca. 25 µM KP-insulin or analogues in 50 mM potassium phosphate (pH 7.4); samples are diluted to 5 µM for guanidine-induced denaturation studies at 25° C. To extract free energies of unfolding, denaturation transitions are fitted by non-linear least squares to a two-state model as described by Sosnick et al., *Methods Enzymol.* 317: 393-409. In brief, CD data θ(x), where x indicates the concentration of denaturant, are fitted by a nonlinear least-squares program according to $$\theta(x) = \frac{\theta_A + \theta_B e^{(-\Delta G^0_{H_2O} - mx)/RT}}{1 + e^{-(\Delta G^0_{H_2O} - mx)/RT}}$$

where x is the concentration of guanidine and where $\theta_A$ and $\theta_B$ are baseline values in the native and unfolded states. Baselines are approximated by pre- and post-transition lines $\theta_A(x) = \theta_A^{H_2O} + m_A x$ and $\theta_B(x) = \theta_B^{H_2O} + m_B x$.

Relative activity is defined as the ratio of analogue to wild-type human insulin required to displace 50 percent of specifically bound $^{125}$I-human insulin. A human placental membrane preparation containing the insulin receptor (IR) is employed, as known in the art. Membrane fragments (0.025 mg protein/tube) were incubated with $^{125}$I-labeled insulin (ca. 30,000 cpm) in the presence of selected concentrations of unlabelled analogue for 18 hours at 4° C. in a final volume of 0.25 ml of 0.05 M Tris-HCl and 0.25 percent (w/v) bovine serum albumin at pH 8. Subsequent to incubation, mixtures are diluted with 1 ml of ice-cold buffer and centrifuged (10,000 g) for 5 min at 4° C. The supernatant is then removed by aspiration, and the membrane pellet counted for radioactivity. Data is corrected for nonspecific binding (amount of radio-activity remaining membrane associated in the presence of 1 µM human insulin. In all assays the percentage of tracer bound in the absence of competing ligand was less than 15% to avoid ligand-depletion artifacts. An additional insulin receptor-binding assay to monitor changes in activity during the course of incubation of the insulin analogue at 37° C. may be performed using a microtiter plate antibody capture as known in the art. Microtiter strip plates (Nunc Maxisorb) are incubated overnight at 4° C. with AU5 IgG (100 µl/well of 40 µg/ml in phosphate-buffered saline). Binding data may be analyzed by a two-site sequential model. A corresponding microtiter plate antibody assay using the IGF Type I receptor may be employed to assess cross-binding to this homologous receptor.

Modified residues were introduced within the context of KP-insulin. Activity values shown are based on ratio of hormone-receptor dissociation constants relative to human insulin; the activity of human insulin is thus 1.0 by definition. Standard errors in the activity values were in general less than 25%. Free energies of unfolding ($\Delta G_u$) at 25° C. were estimated based on a two-state model as extrapolated to zero denaturant concentration. Lag time indicates time (in days) required for initiation of protein fibrillation on gentle agitation at 37° C. in zinc-free phosphate-buffered saline (pH 7.4).

The chlorinated-Phe$^{B24}$ substitution provided herein may be made in insulin analogues such as lispro insulin (that is, an insulin analogue also containing the substitutions Lys$^{B28}$, Pro$^{B29}$ (sold under the name Humalog®)). Such an insulin analogue is designated chlorinated-Phe$^{B24}$-KP-insulin. For comparative purposes, fluorine substitutions were also introduced, essentially as described above, with the exception of para-fluorinated phenylalanine being introduced at positions B24 and B26 in lispro insulin. Analogues containing para-fluorinated phenylalanine substitutions at position B24 are designated 4F-Phe$^{B24}$-KP-insulin. Analogues containing para-fluorinated phenylalanine substitutions at position B26 (substituting for tyrosine) are designated 4F-Phe$^{B26}$-KP-insulin. Designations of respective analogues of KP-insulin and DKP-insulin may be abbreviated in tables and figures as KP and DKP with "insulin" omitted for brevity.

For chlorinated phenylalanine substitutions at B24, a synthetic octapeptide representing residues (N)-GF*FYTKPT (chlorinated phenylalanine residue indicated as "F*" and "KP" substitutions (underlined); SEQ ID NO: 9) and truncated analogue des-octapeptide[B23-B30]-insulin (wild type at position B10, SEQ ID NO: 15) were used. For fluorinated phenylalanine substitutions at B26, a synthetic octapeptide representing residues (N)-GFFF*TKPT (fluorinated phenylalanine indicated again as "F*" and "KP" substitutions (underlined); SEQ ID NO: 16) and truncated analogue des-octapeptide[B23-B30]-insulin (SEQ ID NO: 15) were used.

The resulting data for substitution of a halogenated phenylalanine at position B24 or B26 in a lispro insulin analogue background are presented below in Table 1.

TABLE 1

Stability And Activity Of Halogenated-Phe Analogues Of Lispro Insulin

| Sample | $\Delta G_u$ (Kcal/mol) | $\Delta\Delta G_u$ (Kcal/mol) | $C_{mid}$ (M Gu-HCl) | m (Kcal/mol/M) | receptor binding (%) |
|---|---|---|---|---|---|
| KP-insulin | 3.0 ± 0.06 | / | 4.5 ± 0.1 | 0.61 ± 0.01 | 92 |
| 4F-Phe$^{B24}$-KP | 2.75 ± 0.1 | 0.05 ± 0.16 | 4.4 ± 0.1 | 0.62 ± 0.02 | 32 |
| 4F-Phe$^{B26}$-KP | 3.7 ± 0.1 | 0.9 ± 0.16 | 4.9 ± 0.2 | 0.75 ± 0.02 | 13 |
| 4Cl-Phe$^{B24}$-KP | 2.6 +/− 0.1 | 0.4 ± 0.2 | 4.7 +/− 0.2 | 0.58 +/− 0.02 | 90-100 |

Fibrillation Assays. The physical stability of 4Cl-Phe$^{B24}$-KP-insulin was evaluated in triplicate during incubation in zinc-free phosphate-buffered saline (PBS) at pH 7.4 at 37° C. under gentle agitation in glass vials. The samples were observed for 12 days at a protein concentration of 60 μM for visual appearance of cloudiness; twice daily aliquots were withdrawn for analysis of thioflavin-T (ThT) fluorescence. Because ThT fluorescence is negligible in the absence of amyloid but is markedly enhanced on onset of fibrillation, this assay probes for the lag time. Respective lag times for human insulin, KP-insulin, and 4Cl-Phe$^{B24}$-KP-insulin are 5±1 days, 3±1 days, and more than 12 days. 4Cl-Phe$^{B24}$-KP-insulin is therefore at least 4-fold more resistant to fibrillation under these conditions than is KP-insulin and at least 2-fold more resistant than human insulin. While not wishing to condition patentability on theory, it is envisioned that increased fibrillation resistance of 4Cl-Phe$^{B24}$ insulin analogues will allow them to be formulated in a zinc-free formulation to enhance the fast-acting nature of the insulin analogue without significantly shortening the storage time of a sample of the analogue, either before or after an individual sample has begun to be used.

Thermodynamic Stability. We measured the free energy of unfolding of 4Cl-Phe$^{B24}$-KP-insulin relative to KP-insulin and LysA8-KP-insulin in a zinc-free buffer at pH 7.4 and 25° C. (10 mM potassium phosphate and 50 mM KCl). This assay utilized CD detection of guanidine-induced denaturation as probed at helix-sensitive wavelength 222 nm Values of ΔGu were extrapolated to zero denaturant concentration to obtain estimates by the free energy of unfolding on the basis of a two-state model. Whereas the substitution ThrA8→Lys augmented thermodynamic stability by 0.6±0.2 kcal/mole, the 4Cl-Phe$^{B24}$ modification decreased stability by 0.4±0.2 kcal/mole.

Figure 3A:
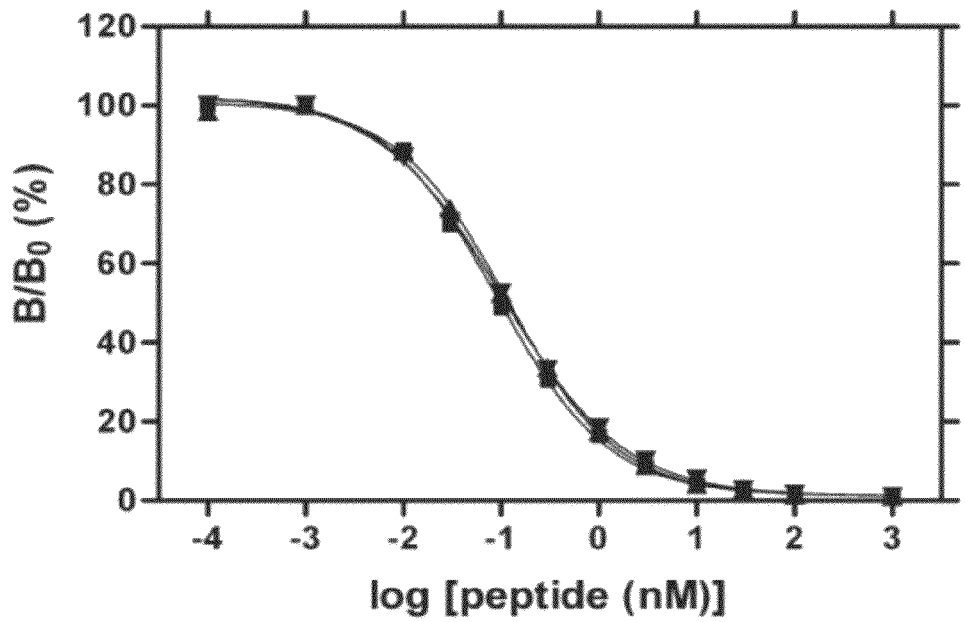
FIG. 3A is a graph showing the results of in vitro receptor-binding assays using isolated insulin receptor (isoform B): human insulin (triangles), KP-insulin (squares), and 4Cl-$Phe^{B24}$-KP-insulin (inverted triangles).

The affinity of 4Cl-Phe$^{B24}$-KP-insulin-A8T for the detergent-solubilized and lectin purified insulin receptor (isoform B) is similar to that of human insulin. A competitive displacement assay using $^{125}$I-labeled human insulin as tracer is shown in FIG. 3A using isolated insulin receptor (isoform B): human insulin (triangles), KP-insulin (squares), 4Cl-Phe$^{B24}$-KP-insulin (inverted triangles). All three curves are closely aligned, indicating similar receptor-binding affinities. The affinity of 4Cl-Phe$^{B24}$-KP-insulin for the insulin receptor was indistinguishable from that of KP-human insulin, in each case slightly lower than the affinity of wild-type insulin.

Figure 3B:
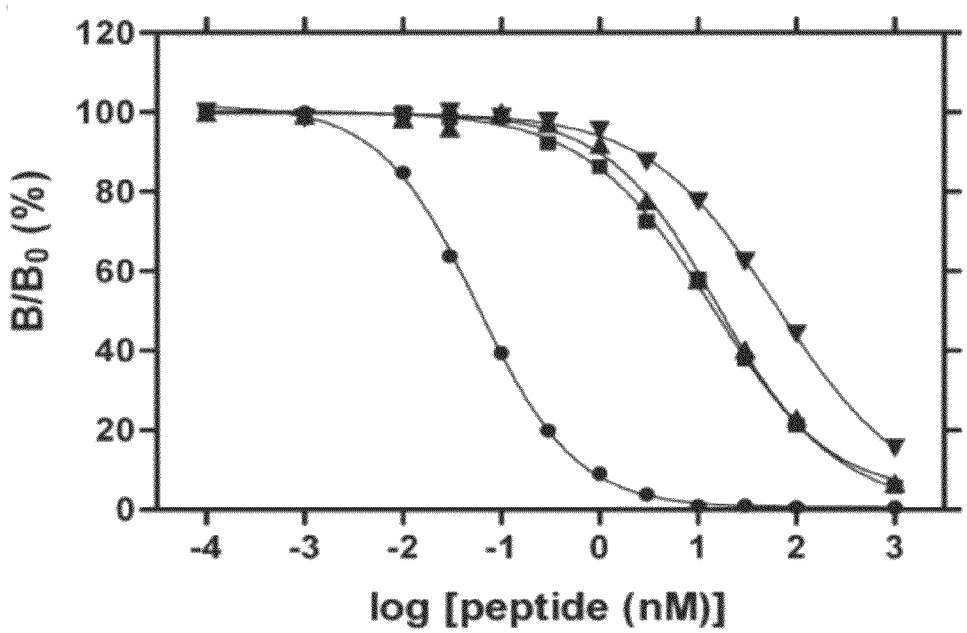
FIG. 3B is a graph showing the results of in vitro receptor-binding assays employing IGF-1R: human insulin (triangles), KP-insulin (squares), 4Cl-$Phe^{B24}$-KP-insulin (inverted triangles), and native IGF-I (circles).

FIG. 3B shows results of corresponding assays employing Insulin-like Growth Factor I Receptor (IGF-1R), probed by competitive displacement using $^{125}$I-labeled IGF-I as tracer. Symbols are the same with the addition of native IGF-I (circles). The rightward shift of the 4Cl-Phe$^{B24}$-KP-insulin curve indicates decreased cross-binding to IGF-1R. The cross-binding of 4Cl-Phe$^{B24}$-KP-insulin to IGF-1R is reduced by approximately 3-fold relative to that of KP-insulin or wild-type insulin.

Figure 3C:
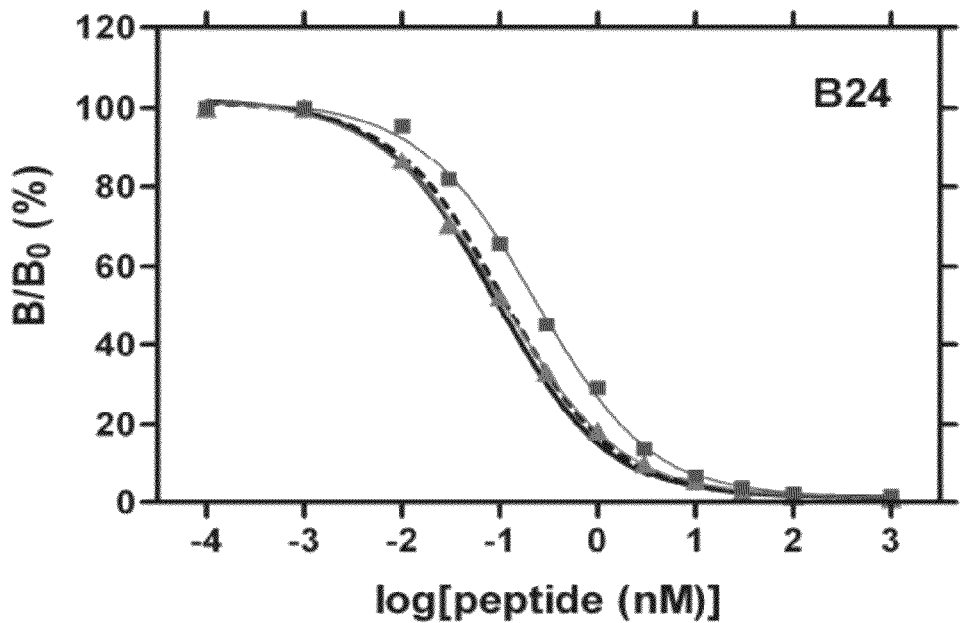
FIG. 3C is a graph comparing the results of in vitro receptor-binding assays using isolated insulin receptor (isoform B): human insulin (solid line), KP-insulin (dashed line), 4Cl-Phe$^{B24}$-KP-insulin (triangles) 4F-Phe$^{B24}$-KP-insulin (squares).

A similar comparison between human insulin (solid black line), KP-insulin (dashed line), 4Cl-Phe$^{B24}$-KP-insulin (triangles), 4F-Phe$^{B24}$-KP-insulin (squares) using isolated insulin receptor (isoform B), is shown in FIG. 3C. The rightward shift of the 4F-Phe$^{B24}$-KP-insulin curve relative to 4Cl-Phe$^{B24}$-KP-insulin, wild type human insulin and lispro insulin shows decreased receptor-binding affinity with the use of a different halogen at the same position on the phenylalanine ring in comparison to a para-chloro substitution of the phenylalanine at B24. In contrast, the insulin receptor-binding affinity of 4Cl-Phe$^{B24}$-KP-insulin is similar to that of wild type human insulin and lispro (KP) insulin.

Figure 3D:
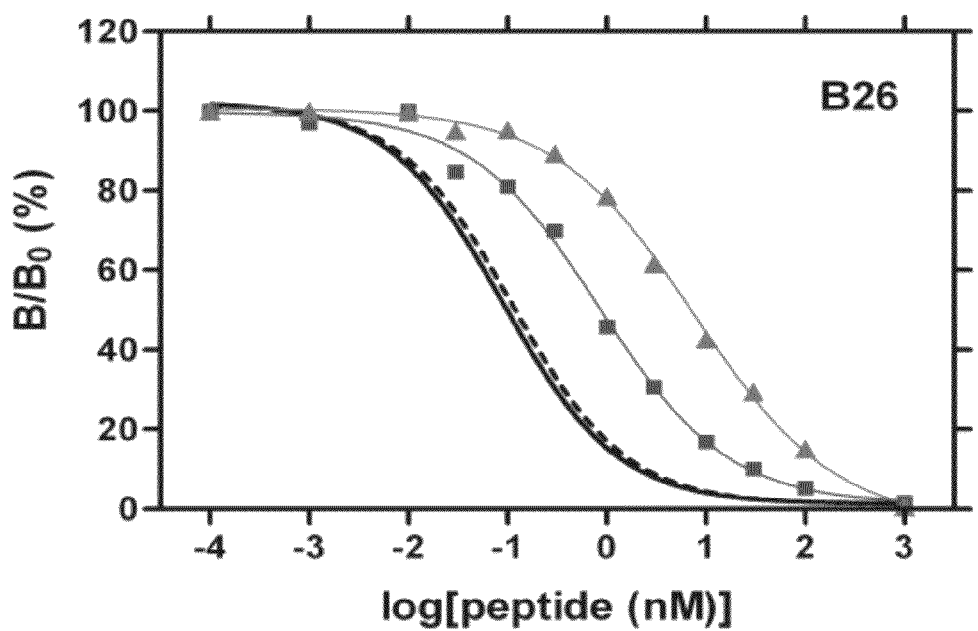
FIG. 3D is a graph comparing the results of in vitro receptor-binding assays using isolated insulin receptor (isoform B): human insulin (solid line), KP-insulin (dashed line), 4Cl-Phe$^{B26}$-KP-insulin (triangles) 4F-Phe$^{B26}$-KP-insulin (squares).

A further comparison between human insulin (solid line), KP-insulin (dashed line), 4Cl-Phe$^{B26}$-KP-insulin (triangles) 4F-Phe$^{B26}$-KP-insulin (squares) using isolated insulin receptor (isoform B), is shown in FIG. 3D. Both 4Cl-Phe$^{B26}$-insulin and 4F-Phe$^{B26}$-KP-insulin show decreased insulin receptor-binding affinity in comparison to wild type and lispro insulins. As stated above, 4Cl-Phe$^{B24}$-KP-insulin does not show a similar decrease in receptor-binding affinity.

Figure 4:
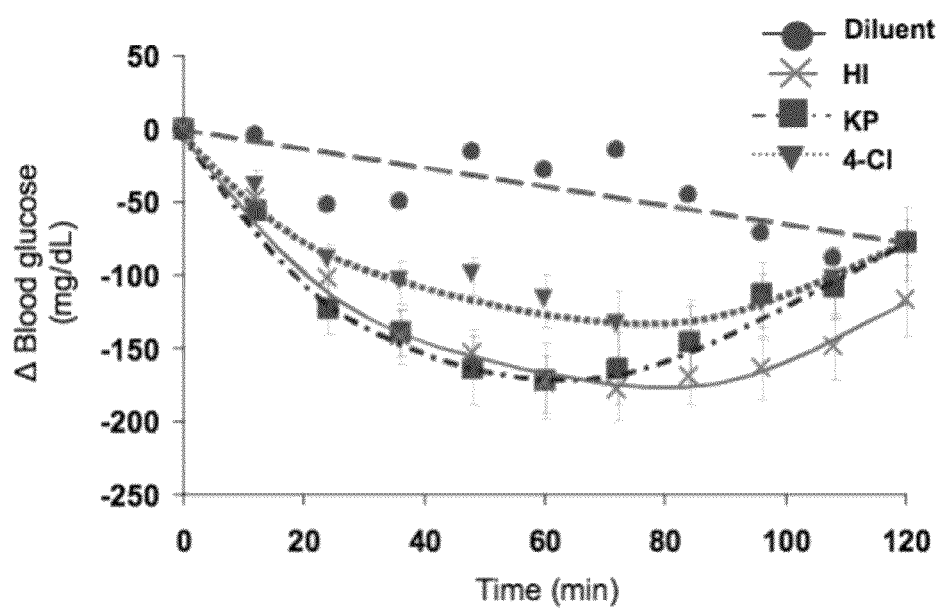
FIG. 4 is a graph showing the hypoglycemic action of subcutaneous of 4Cl-Phe$^{B24}$-KP-insulin in STZ induced diabetic Lewis rats over time (inverted triangles) relative to diluent alone (circles), human insulin (crosses), and KP-insulin (squares).

The in vivo potency of 4Cl-Phe$^{B24}$-KP-insulin in diabetic rats is similar to that of KP-insulin. To enable characterization of biological activity, male Lewis rats (~300 g body weight) were rendered diabetic with streptozotocin. Human insulin, KP-insulin, and 4Cl-Phe$^{B24}$-KP-insulin were purified by HPLC, dried to powder, and dissolved in insulin diluent (Eli Lilly Corp). Rats were injected subcutaneously at time=0 with either 20 μg or 6.7 μg of KP-insulin or 4Cl-Phe$^{B24}$-KP-insulin in 100 nl of diluent; the higher dose is at the plateau of the wild-type insulin dose-response curve whereas the lower dose corresponds to 50-70% maximal initial rate of glucose disposal. Injection of diluent alone was performed as a negative control. 8 rats were studies in each group. Blood was obtained from clipped tip of the tail at time 0 and at successive intervals up to 120 min Blood glucose was measured using a Hypoguard Advance Micro-Draw meter. Blood glucose concentrations were observed to decrease as shown in FIG. 4. The initial rate of fall of the blood glucose concentration during the first 24 min after injection are similar on comparison of 4Cl-Phe$^{B24}$-KP-insulin (−225±29 mg/dl/h), KP-insulin (−256±35 mg/dl/h), and human insulin (−255±35 mg/dl/h). Any differences in initial rate are not statistically significant. The duration of action of 4Cl-Phe$^{B24}$-KP-insulin over the next 60 min appears shorter, however, than the durations of human insulin or KP-insulin.

Given the native receptor-binding affinity of 4Cl-Phe$^{B24}$-KP-insulin, it would be unusual for its potency to be less than that of human insulin. Indeed, insulin analogs with relative affinities in the range 30-100% relative to wild-type typically exhibit native potencies in vivo. It is formally possible, however, that the biological potency of 4Cl-Phe$^{B24}$-KP-insulin is somewhat lower (on a molar basis) than the potencies of human insulin or KP-insulin. If so, we note that any such decrease would be within the threefold range of the molar activities of current insulin products in clinical use (by convention respective international units (IU) are redefined to reflect extent of glucose lowering, leading to product-to-product differences in the number of milligrams or nanomoles per unit). It should be noted that the slow decline in blood glucose concentration on control injection of protein-free diluent (brown dashed line in FIG. 4) reflects diurnal fasting of the animals following injection.

A surrogate marker for the pharmacokinetics of insulin hexamer disassembly (designated the EDTA sequestration assay) employs cobalt ions ($Co^{2+}$) rather than zinc ions ($Zn^{2+}$) to mediate hexamer assembly. Although $Co^{2+}$ and $Zn^{2+}$ hexamers are similar in structure, the cobalt ion provides a convenient spectroscopic probe due to its unfilled d-electronic shell.

The principle of the assay is as follows. Solutions of $R_6$ phenol-stabilized $Co^{2+}$ insulin hexamers are blue due to tetrahedral $Co^{2+}$ coordination; on disassembly the protein solution is colorless as octahedral $Co^{2+}$ coordination by water or EDTA (ethylene-diamine-tetra-acetic acid; a strong chelator of metal ions) lacks optical transitions at visible wavelengths as a consequence of ligand field theory. The EDTA sequestration assay exploits these spectroscopic features as follows. At time t=0 a molar excess of EDTA is added to a solution of $R_6$ insulin hexamers or insulin analog hexamers. Although EDTA does not itself attack the hexamer to strip it of metal ions, any $Co^{2+}$ ions released in the course of transient hexamer disassembly become trapped by the chelator and thus unavailable for reassembly. The rate of disappearance of the blue color (the tetrahedral d-d optical transition at 574 nm of the R-specific insulin-bound $Co^{2+}$) thus provides an optical signature of the kinetics of hexamer disassembly.

Figure 5A:
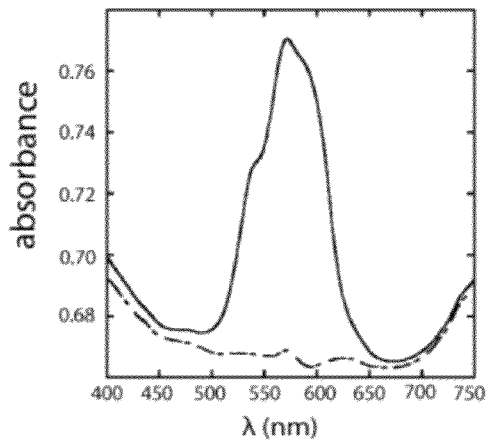
FIGS. 5A-C are graphs showing averaged traces of insulin cobalt solutions showing characteristic spectral profiles from 400-750 nm before and after addition of 2 mM EDTA. Samples were dissolved in 50 mM Tris (pH 7.4), 50 mM phenol, and 0.2 mM CoCl$_2$. NaSCN was then added to a final concentration of 1 mM. Solid lines show data pre-EDTA extraction. Dashed lines show data post-EDTA extraction. Panel A: wild type insulin; Panel B: KP-insulin; Panel C; 4Cl-Phe$^{B24}$-KP-insulin.
Figure 5B:
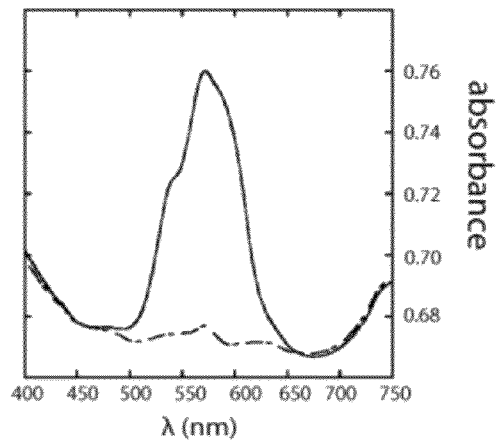
Figure 5C:
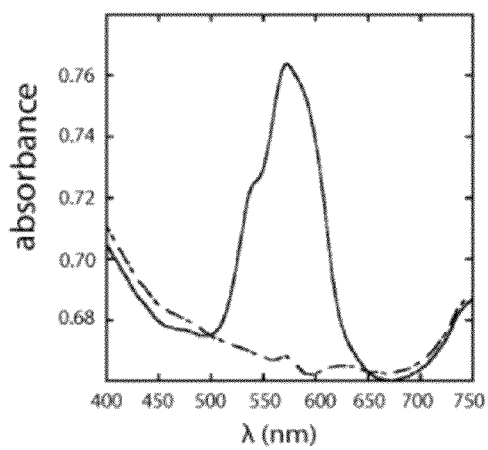

Averaged traces of insulin cobalt solutions showing characteristic spectral profiles from 400-750 nm were determined before and after addition of 2 mM EDTA (FIGS. 5A-C). Samples were dissolved in 50 mM Tris (pH 7.4), 50 mM phenol, and 0.2 mM $CoCl_2$. NaSCN was then added to a final concentration of 1 mM. The kinetics of hexamer dissociation after addition of 2 mM EDTA as monitored at 574 nm (25° C. and pH 7.4) are also shown. The spectra of the analogues before EDTA extraction are shown as solid lines. Post-EDTA extraction, the spectra are displayed as dashed lines. Wild type is shown in Panel A, KP-insulin in Panel B, and 4Cl-$Phe^{B24}$-KP-insulin as in Panel C. Data were normalized to time zero for each sample.

On the one hand, the baseline optical absorption spectra of the hexameric cobalt complexes at t=0 are similar among wild-type insulin hexamers, KP insulin hexamers, and 4Cl-$Phe^{B24}$-KP-insulin hexamers (see FIGS. 5A-5C). The similar shapes and magnitudes of these respective d-d electronic transitions imply that the metal ions are in similar $R_6$-specific tetrahedral coordination sites in wild-type and variant hexamers. This result is significant as it implies that 4Cl-$Phe^{B24}$-KP-insulin remains competent for metal-ion-mediated assembly and hence a zinc-based formulation.

Figure 5D:
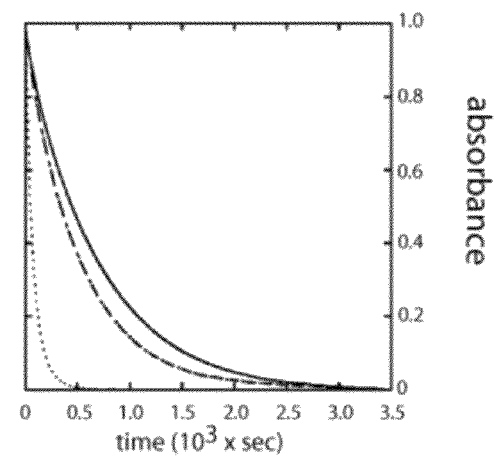
FIG. 5D is a graph showing the kinetics of hexamer dissociation after addition of 2 mM EDTA as monitored at 574 nm (25° C. and pH 7.4). Data were normalized to time zero for each sample: wild type (solid line), KP-insulin (dashed line), and 4Cl-Phe$^{B24}$-KP-insulin (dotted line).
Figure 6:
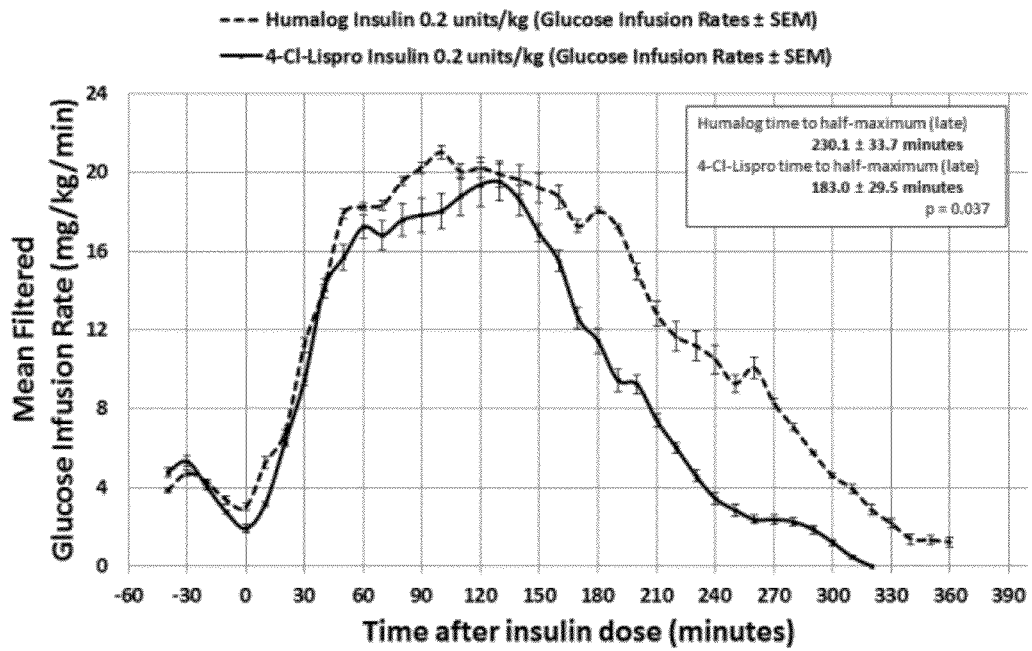
FIG. 6 is a graph showing a plot of the mean filtered glucose infusion rate versus time after insulin dose for KP-insulin (Lispro insulin) and 4Cl-Phe$^{B24}$-KP-insulin (4-Cl-Lispro insulin) at a dosage of 0.2 Units per kilogram of bodyweight.

The kinetics of hexamer dissociation after addition of 2 mM EDTA as monitored at 574 nm (25° C. and pH 7.4) shows that the wild-type and variant hexamers exhibit marked differences in rates of EDTA-mediated $Co^{2+}$ sequestration. As expected, the wild-type hexamer exhibits the greatest kinetic stability (solid line in FIG. 5D), followed by KP-insulin (dashed-dotted line in FIG. 5D), and 4-Cl-PheB24-KP-insuln (dotted line in FIG. 5D). Respective half-lives are 481 sec (wild type), 363 sec (KP-insulin), and 66 sec (4Cl-$Phe^{B24}$-KP-insulin). The extent of acceleration induced by the para-chloro-aromatic substitution is thus more profound than that associated with the "KP switch" of Lispro insulin (Humalog™). Because diffusion of zinc ions from the site of subcutaneous injection is analogous to the in vitro sequestration of colbalt ions in the EDTA Sequestration assay, these findings predict that 4Cl-$Phe^{B24}$-KP-insulin will exhibit a marked acceleration of absorption.

The pharmacokinetic (PK) and pharacodynamic (PD) properties and potency of 4-Cl-$Phe^{B24}$-KP-insulin were investigated in relation to wild-type insulin (Humulin™; Eli Lilly and Co.) and KP-insulin (Humalog™) in adolescent Yorkshire farm pigs (weight 25-45 kg). The wild type and KP-insulin were used as provided by the vendor (Eli Lilly and Co.) in U-100 strength. The 4-Cl-$Phe^{B24}$-KP-insulin was formulated in Lilly diluent with a ratio of protein to zinc ions similar to that of the wild type and KP-insulin products; its strength was U-87. On the day of study, each animal underwent anesthesia induction with Telazol and then general anesthesia with isoflurane. Each animal was endotreacheally intubated, and oxygen saturation and end-tidal expired $CO_2$ were continuously monitored. To block endogenous pancreatic α- and β-cell secretion, pigs were given a subcutaneous injection of octreotide acetate (44 µg/kg) approximately 30 min before beginning the clamp study and every 2 h thereafter. After IV catheters were placed and baseline euglycemia was established with 10% dextrose infusion, an IV injection of the insulin was given through the catheter. In order to quantify peripheral insulin-mediated glucose uptake, a variable-rate glucose infusion was given to maintain a blood glucose concentration of approximately 85 mg/dl. Such a glucose infusion was typically required for 5-8 h until the glucose infusion rate returned to the pre-insulin baseline. Glucose concentrations were measured with a Hemocue 201 portable glucose analyzer every 10 min (instrument error rate: 1.9%). The computerized protocol for glucose clamping was as described by Matthews et al. 2-ml blood samples for insulin assay was also obtained according to the following schedule: from 0-40 min after insulin delivery: 5-minute intervals; from 50-140 min: 10-minute intervals, and from 160 min-to the point when GIR is back to baseline: 20-min intervals. For analysis of PK/PD, a 20-min moving mean curve fit and filter was applied. PD was measured as time to early half-maximal effect (½ $T_{max}$ Early), time to late half-maximal effect (½ $T_{max}$ Late), time to maximal effect, and area-under-the-curve (AUC) over baseline. For each of these analyses, the fitted curve, not the raw data, was used. Each of 3 pigs underwent 3 studies. The results of these studies are provided in FIGS. 6-9.

4-Cl-$Phe^{B24}$-KP-insulin (abbreviated in FIG. 6 as 4-Cl-Lispro Insulin) was found to exhibit a significantly less prolonged late "tail" than KP-insulin or wild-type insulin. The improved turn-off of insulin action suggests a potential clinical benefit with regard to late post-prandial hypoglycemia.

Figure 7:
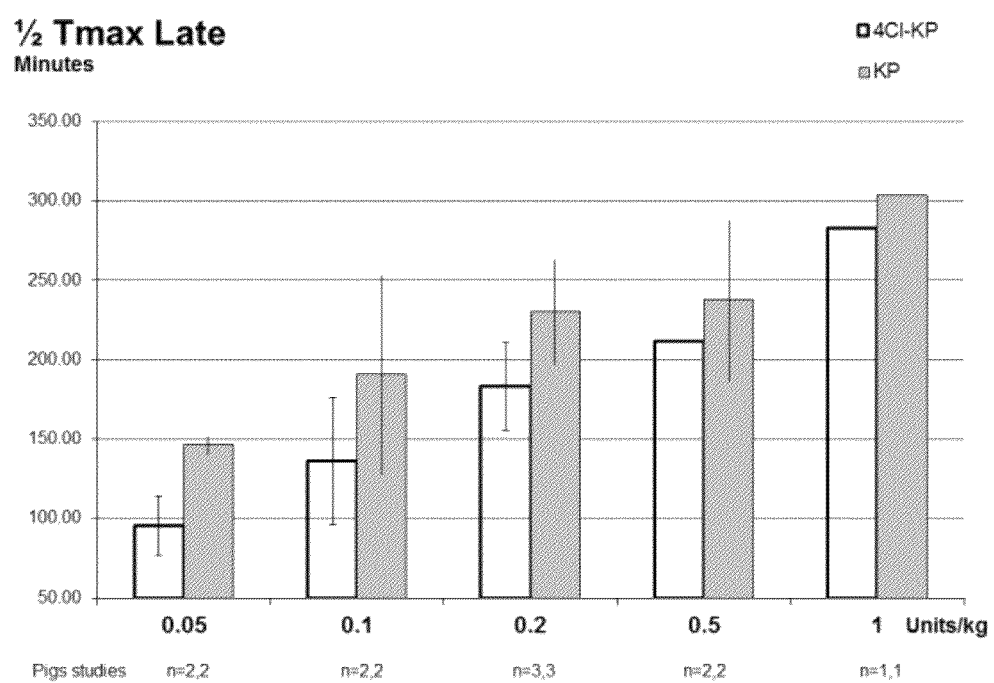
FIG. 7 is a bar graph summarizing 20 pharmacodynamic studies in pigs demonstrating significant improvement in ½ T-max late in 4Cl-Phe$^{B24}$-KP-insulin over KP-insulin at five different dosing levels.

FIG. 7 summarizes 20 pharmacodynamic studies in pigs demonstrating significant improvement in ½ T-max late in 4-Cl-$Phe^{B24}$-KP-insulin over KP-insulin at five different dosing levels, 0.05 U/kg, 0.1 U/kg, 0.2 U/kg, 0.5 U/kg, and 1 U/kg.

Figure 8:
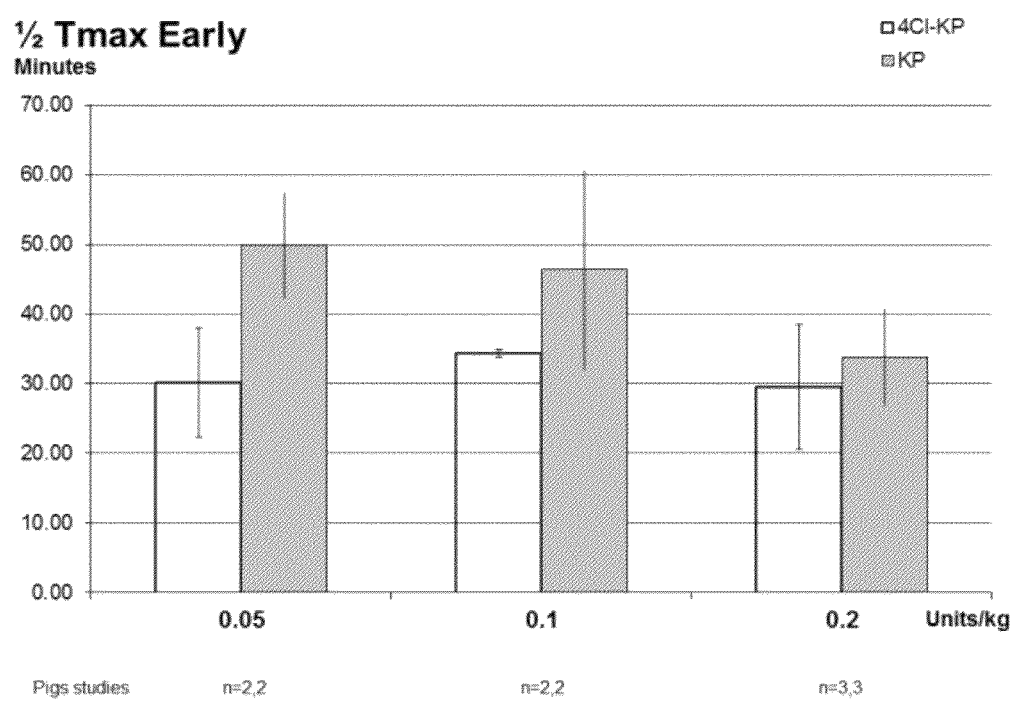
FIG. 8 is a bar graph summarizing 14 pharmacodynamic studies in pigs suggesting improvement in ½ T-max early in 4Cl-Phe$^{B24}$-KP-insulin over KP-insulin at three different dosing levels.

FIG. 8 summarizes 14 pharmacodynamic studies in pigs suggesting improvement in ½ T-max early in 4-Cl-$Phe^{B24}$-KP-insulin over KP-insulin at three different dosing levels, 0.05 U/kg, 0.1 U/kg, 0.2 U/kg.

Figure 9:
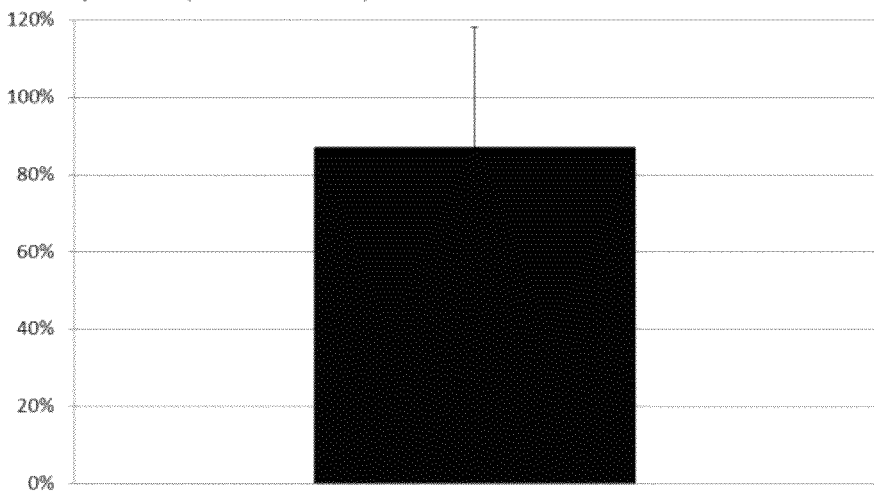
FIG. 9 is a summary of ten, matched pharmacodynamics studies comparing the relative potencies 4Cl-Phe$^{B24}$-KP-insulin with that of KP insulin as measured by area under the curve (AUC) in which the slightly reduced average potency for 4-Cl-KP was found not to be statistically significant (p=0.22).

FIG. 9 summarizes ten, matched pharmacodynamics studies comparing the relative potencies 4Cl-$Phe^{B24}$-KP-insulin with that of KP insulin as measured by area under the curve (AUC) in which the slightly reduced average potency for 4-Cl-KP was found not to be statistically significant (p=0.22). The pharmacokinetic (PK) and pharmacodynamic (PD) properties of 4-Cl-$Phe^{B24}$-KP-insulin in relation to wild-type insulin and KP-insulin (Lispro-insulin) under similar formulation conditions (zinc insulin hexamers or zinc insulin analog hexamers stabilized by phenol and meta-cresol) show that the potency of 4-Cl-$Phe^{B24}$-KP-insulin, as measured by area-under-the-curve (AUC) method, was similar to those of wild-type insulin and KP-insulin.

A method for treating a patient comprises administering a chlorinated-$Phe^{B24}$ substituted insulin analogue to the patient. In one example, the insulin analogue is a 4Cl-$Phe^{B24}$-KP insulin. The insulin analogue may optionally contain a histidine, lysine or arginine substitution at position A8. In another example, the chlorine-substituted insulin analogue additionally contains one or more substitutions elsewhere in the insulin molecule designed to alter the rate of action of the analogue in the body. In still another example, the insulin analogue is administered by an external or implantable insulin pump. An insulin analogue of the present invention may also contain other modifications, such as a tether between the C-terminus of the B-chain and the N-terminus of the A-chain as described more fully in co-pending U.S. patent application Ser. No. 12/419,169.

A pharmaceutical composition may comprise such insulin analogues and may optionally include zinc Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin® (Eli Lilly and Co.), Humalog® (Eli Lilly and Co.), Novalin® (Novo-Nordisk), and Novalog® (Novo-Nordisk) and other rapid-acting insulin formulations currently approved for human use, (b) "NPH" formulations of the above and other insulin analogues, and (c) mixtures of such formulations. As mentioned above, it is believed that the increased resistance to fibrillation will permit 4Cl-Phe$^{B24}$-containing insulin analogues to be formulated without the presence of zinc to maximize the fast acting nature of the analogue. However, it is also believed that even in the presence of zinc, the 4Cl-Phe$^{B24}$-containing insulin analogues will dissociate from hexamers into dimers and monomers sufficiently quickly as to also be considered a fast-acting insulin analogue formulation.

Excipients may include glycerol, glycine, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

A nucleic acid comprising a sequence that encodes a polypeptide encoding an insulin analogue containing a sequence encoding at least a B-chain of insulin with a chlorinated phenylalanine at position B24 is also envisioned. This can be accomplished through the introduction of a stop codon (such as the amber codon, TAG) at position B24 in conjunction with a suppressor tRNA (an amber suppressor when an amber codon is used) and a corresponding tRNA synthetase, which incorporates a non-standard amino acid into a polypeptide in response to the stop codon, as previously described (Futter, 1998, *Protein Sci.* 7:419-426; Xie et al., 2005, *Methods.* 36: 227-238). The particular sequence may depend on the preferred codon usage of a species in which the nucleic acid sequence will be introduced. The nucleic acid may also encode other modifications of wild-type insulin. The nucleic acid sequence may encode a modified A- or B-chain sequence containing an unrelated substitution or extension elsewhere in the polypeptide or modified proinsulin analogues. The nucleic acid may also be a portion of an expression vector, and that vector may be inserted into a host cell such as a prokaryotic host cell like an *E. coli* cell line, or a eukaryotic cell line such as *S. cereviciae* or *Pischia pastoris* strain or cell line.

For example, it is envisioned that synthetic genes may be synthesized to direct the expression of a B-chain polypeptide in yeast *Piscia pastoris* and other microorganisms. The nucleotide sequence of a B-chain polypeptide utilizing a stop codon at position B24 for the purpose of incorporating a chlorinated phenylalanine at that position may be either of the following or variants thereof:
(a) with Human Codon Preferences:

```
                                           (SEQ ID NO: 11)
TTTGTGAACCAACACCTGTGCGGCTCACACCTGGTGGAAGCTCTCTACC

TAGTGTGCGGGAACGAGGCTAGTTCTACACACCCAAGACC
```

(b) with *Pichia* Codon Preferences:

```
                                           (SEQ ID NO: 12)
TTTGTTAACCAACATTTGTGTGGTTCTCATTTGGTTGAAGCTTTGTACT

TGGTTTGTGGTGAAAGAGGTTAGTTTTACACTCCAAAGACT
```

Similarly, a full length pro-insulin cDNA having human codon preferences and utilizing a stop codon at position B24 for the purpose of incorporating a chlorinated phenylalanine at that position may have the sequence of SEQ ID NO: 13.

```
                                           (SEQ ID NO: 13)
TTTGTGAACC AACACCTGTG CGGCTCACAC CTGGTGGAAG

CTCTCTACCT AGTGTGCGGG AACGAGGCT AGTTCTACAC

ACCCAAGACC CGCCGGGAGG CAGAGGACCT GCAGGTGGGG

CAGGTGGAGC TGGGCGGCGG CCCTGGTGCA GGCAGCCTGC

AGCCCTTGGC CCTGGAGGGG TCCCTGCAGA AGCGTGGCAT

TGTGGAACAA TGCTGTACCA GCATCTGCTC CCTCTACCAG

CTGGAGAACT ACTGCAACTA G
```

Likewise, a full length human pro-insulin cDNA utilizing a stop codon at position B24 for the purpose of incorporating a chlorinated phenylalanine at that position and having codons preferred by *P. pastoris* may have the sequence of SEQ ID NO: 14

```
                                           (SEQ ID NO: 14)
TTTGTTAACC AACATTTGTG TGGTTCTCAT TTGGTTGAAG

CTTTGTACTT GGTTTGTGGT GAAAGAGGTT AGTTTTACAC

TCCAAAGACT AGAAGAGAAG CTGAAGATTT GCAAGTTGGT

CAAGTTGAAT TGGGTGGTGG TCCAGGTGCT GGTTCTTTGC

AACCATTGGC TTTGGAAGGT TCTTTGCAAA AGAGAGGTAT

TGTTGAACAA TGTTGTACTT CTATTTGTTC TTTGTACCAA

TTGGAAAACT ACTGTAACTA A
```

Based upon the foregoing disclosure, it should now be apparent that chlorine-substituted insulin analogues will carry out the objects set forth hereinabove. Namely, these insulin analogues exhibit enhanced thermodynamic stability, resistance to fibrillation and potency in reducing blood glucose levels. The chlorine substituted phenylalanine-containing insulin analogues also have reduced cross-reactivity to insulin-like growth factor (IGFR). It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Furter, R., 1998. Expansion of the genetic code: Site-directed p-fluoro-phenylalanine incorporation in *Escherichia coli*. *Protein Sci.* 7:419-426.

Matthews D. R., Hosker J. P. 1989. Unbiased and flexible iterative computer program to achieve glucose clamping. *Diabetes Care.* 12: 156-9.

Merrifield, R. B., Vizioli, L. D., and Boman, H. G. 1982. Synthesis of the antibacterial peptide cecropin A (1-33). *Biochemistry* 21: 5020-5031.

Mirmira, R. G., and Tager, H. S. 1989. Role of the phenylalanine B24 side chain in directing insulin interaction with its receptor: Importance of main chain conformation. *J. Biol. Chem.* 264: 6349-6354.

Sosnick, T. R., Fang, X., and Shelton, V. M. 2000. Application of circular dichroism to study RNA folding transitions. *Methods Enzymol.* 317: 393-409.

Wang, Z. X. 1995. An exact mathematical expression for describing competitive biding of two different ligands to a protein molecule *FEBS Lett.* 360: 111-114.

Weiss, M. A., Hua, Q. X., Jia, W., Chu, Y. C., Wang, R. Y., and Katsoyannis, P. G. 2000. Hierarchiacal protein "un-design": insulin's intrachain disulfide bridge tethers a recognition α-helix. *Biochemistry* 39: 15429-15440.

Whittaker, J., and Whittaker, L. 2005. Characterization of the functional insulin binding epitopes of the full length insulin receptor. *J. Biol. Chem.* 280: 20932-20936.

Xie, J. and Schultz, P. G. 2005. An expanding genetic code. *Methods.* 36: 227-238.

What is claimed is:

1. An insulin analogue comprising a B-chain polypeptide incorporating a chlorinated phenylalanine, wherein the analogue displays at least one property, compared to a corresponding insulin analogue that contains a non-chlorinated phenylalanine, selected from the group consisting of:
improved resistance to fibril formation at room temperature;
at least two-fold improved resistance to fibril formation at room temperature in a zinc-free solution;
decreased cross-binding to Insulin-Like Growth Factor 1 Receptor;
accelerated rate of hexamer disassembly; and
at least 30 percent of the affinity to insulin receptor.

2. The insulin analogue of claim 1, wherein the chlorinated phenylalanine is located at position B24.

3. The insulin analogue of claim 2, wherein the chlorinated phenylalanine is para-monochloro-phenylalanine.

4. The insulin analogue of claim 3, wherein the analogue is an analogue of a mammalian insulin.

5. The insulin analogue of claim 4, wherein the analogue is an analogue of human insulin.

6. The insulin analogue of claim 4, wherein the analogue comprises an amino acid sequence selected from the group consisting of SEQ ID NOS: 4-8 and polypeptides having three or fewer additional amino acid substitutions thereof.

7. The insulin analogue of claim 1, wherein the analogue is an analogue of a mammalian insulin.

8. The insulin analogue of claim 1, wherein the insulin analogue displays improved resistance to fibril formation at room temperature compared to a corresponding insulin analogue that contains a non-chlorinated phenylalanine.

9. The insulin analogue of claim 1, wherein the insulin analogue displays at least two-fold improved resistance to fibril formation at room temperature compared to a corresponding insulin analogue that contains a non-chlorinated phenylalanine.

10. The insulin analogue of claim 1, wherein the insulin analogue displays at least two-fold improved resistance to fibril formation at room temperature in a zinc-free solution compared to a corresponding insulin analogue that contains a non-chlorinated phenylalanine.

11. The insulin analogue of claim 1, wherein the insulin analogue displays decreased cross-binding to Insulin-Like Growth Factor 1 Receptor compared to a corresponding insulin analogue that contains a non-chlorinated phenylalanine.

12. The insulin analogue of claim 1, wherein the insulin analogue displays decreased cross-binding to Insulin-Like Growth Factor 1 Receptor compared to a corresponding wild type insulin.

13. The insulin analogue of claim 1, wherein the insulin analogue displays an accelerated rate of hexamer disassembly compared to a corresponding insulin analogue that contains a non-chlorinated phenylalanine.

14. The insulin analogue of claim 1, wherein the insulin analogue displays at least 30 percent of the affinity to insulin receptor compared to a corresponding wild type insulin.

15. The insulin analogue of claim 1, wherein the analogue displays two or more properties, compared to a corresponding insulin analogue that contains a non-chlorinated phenylalanine, selected from the group consisting of:
   improved resistance to fibril formation at room temperature;
   at least two-fold improved resistance to fibril formation at room temperature in a zinc-free solution;
   decreased cross-binding to Insulin-Like Growth Factor 1 Receptor;
   accelerated rate of hexamer disassembly; and
   at least 30 percent of the affinity to insulin receptor.

16. A method of lowering the blood sugar level of a patient comprising administering a physiologically effective amount of an insulin analogue or a physiologically acceptable salt thereof to the patient, wherein the insulin analogue or a physiologically acceptable salt thereof contains a B-chain polypeptide incorporating a chlorinated phenylalanine, wherein the analogue displays at least one property, compared to a corresponding insulin analogue that contains a non-chlorinated phenylalanine, selected from the group consisting of:
   improved resistance to fibril formation at room temperature;
   at least two-fold improved resistance to fibril formation at room temperature in a zinc-free solution;
   decreased cross-binding to Insulin-Like Growth Factor 1 Receptor;
   accelerated rate of hexamer disassembly; and
   at least 30 percent of the affinity to insulin receptor.

17. The method of claim 16, wherein the chlorinated phenylalanine is located at position B24.

18. The method of claim 17, wherein the chlorinated phenylalanine is para-monochloro-phenylalanine.

19. The method of claim 18, wherein the analogue comprises an amino acid sequence selected from the group consisting of SEQ. ID. NOS. 4-8 and polypeptides having three or fewer additional amino acid substitutions thereof.

* * * * *

SEQUENCE LISTING

```
<160> NUMBER OF SEQ ID NOS: 16

<210> SEQ ID NO 1
<211> LENGTH: 86
<212> TYPE: PRT
<213> ORGANISM: HomoSapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: HomoSapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: HomoSapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: HomoSapiens
<220> FEATURE:
<221> NAME/KEY: MISC_FEATURE
<222> LOCATION: (24)..(24)
<223> OTHER INFORMATION: Xaa=Phe or 4Cl-Phe

<400> SEQUENCE: 4

Phe Val Asn Gln His Leu Cys Gly Ser His Leu Val Glu Ala Leu Tyr
```

```
                1               5                  10                  15
Leu Val Cys Gly Glu Arg Gly Xaa Phe Tyr Thr Lys Pro Thr
                    20                  25                  30

<210> SEQ ID NO 5
<211> LENGTH: 30
<212> TYPE: PRT
<213> ORGANISM: HomoSapiens
<220> FEATURE:
<221> NAME/KEY: MISC_FEATURE
<222> LOCATION: (24)..(24)
<223> OTHER INFORMATION: Xaa=Phe or 4Cl-Phe

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Asp Lys Thr
                    20                  25                  30

<210> SEQ ID NO 6
<211> LENGTH: 52
<212> TYPE: PRT
<213> ORGANISM: HomoSapiens
<220> FEATURE:
<221> NAME/KEY: MISC_FEATURE
<222> LOCATION: (1)..(1)
<223> OTHER INFORMATION: Xaa=His or Phe
<220> FEATURE:
<221> NAME/KEY: MISC_FEATURE
<222> LOCATION: (24)..(24)
<223> OTHER INFORMATION: Xaa=Phe or 4Cl-Phe
<220> FEATURE:
<221> NAME/KEY: MISC_FEATURE
<222> LOCATION: (26)..(26)
<223> OTHER INFORMATION: Xaa=Tyr or Phe
<220> FEATURE:
<221> NAME/KEY: MISC_FEATURE
<222> LOCATION: (28)..(28)
<223> OTHER INFORMATION: Xaa=Pro, Lys or Asp
<220> FEATURE:
<221> NAME/KEY: MISC_FEATURE
<222> LOCATION: (29)..(29)
<223> OTHER INFORMATION: Xaa=Lys or Pro
<220> FEATURE:
<221> NAME/KEY: MISC_FEATURE
<222> LOCATION: (31)..(31)
<223> OTHER INFORMATION: Xaa=0-35 of any amino acid or a break in the
      amino acid chain
<220> FEATURE:
<221> NAME/KEY: MISC_FEATURE
<222> LOCATION: (35)..(35)
<223> OTHER INFORMATION: Xaa=His or Glu
<220> FEATURE:
<221> NAME/KEY: MISC_FEATURE
<222> LOCATION: (39)..(39)
<223> OTHER INFORMATION: Xaa=His or Thr

<400> SEQUENCE: 6

Xaa Val Asn Gln His Leu Cys Gly Ser His Leu Val Glu Ala Leu Tyr
1               5                   10                  15

Leu Val Cys Gly Glu Arg Gly Xaa Phe Xaa Thr Xaa Xaa Thr Xaa Gly
                    20                  25                  30

Ile Val Xaa Gln Cys Cys Xaa Ser Ile Cys Ser Leu Tyr Gln Leu Glu
            35                  40                  45

Asn Tyr Cys Asn
        50

<210> SEQ ID NO 7
<211> LENGTH: 21
```

```
<212> TYPE: PRT
<213> ORGANISM: HomoSapiens
<220> FEATURE:
<221> NAME/KEY: MISC_FEATURE
<222> LOCATION: (8)..(8)
<223> OTHER INFORMATION: Xaa=His, Arg or Lys

<400> SEQUENCE: 7

Gly Ile Val Glu Gln Cys Cys Xaa Ser Ile Cys Ser Leu Tyr Gln Leu
1               5                   10                  15

Glu Asn Tyr Cys Asn
            20

<210> SEQ ID NO 8
<211> LENGTH: 30
<212> TYPE: PRT
<213> ORGANISM: HomoSapiens
<220> FEATURE:
<221> NAME/KEY: MISC_FEATURE
<222> LOCATION: (24)..(24)
<223> OTHER INFORMATION: Xaa=Phe or 4Cl-Phe

<400> SEQUENCE: 8

Phe Val Asn Gln His Leu Cys Gly Ser Asp Leu Val Glu Ala Leu Tyr
1               5                   10                  15

Leu Val Cys Gly Glu Arg Gly Xaa Phe Thr Thr Lys Pro Thr
            20                  25                  30

<210> SEQ ID NO 9
<211> LENGTH: 8
<212> TYPE: PRT
<213> ORGANISM: HomoSapiens
<220> FEATURE:
<221> NAME/KEY: MISC_FEATURE
<222> LOCATION: (2)..(2)
<223> OTHER INFORMATION: Xaa=Phe or 4Cl-Phe

<400> SEQUENCE: 9

Gly Xaa Phe Tyr Thr Lys Pro Thr
1               5

<210> SEQ ID NO 10
<211> LENGTH: 8
<212> TYPE: PRT
<213> ORGANISM: HomoSapiens

<400> SEQUENCE: 10

Gly Phe Phe Tyr Thr Pro Lys Thr
1               5

<210> SEQ ID NO 11
<211> LENGTH: 90
<212> TYPE: DNA
<213> ORGANISM: HomoSapiens

<400> SEQUENCE: 11
tttgtgaacc aacacctgtg cggctcacac ctggtggaag ctctctacct agtgtgcggg      60
gaacgaggct agttctacac acccaagacc                                      90

<210> SEQ ID NO 12
<211> LENGTH: 90
<212> TYPE: DNA
<213> ORGANISM: HomoSapiens

<400> SEQUENCE: 12
```

```
tttgttaacc aacatttgtg tggttctcat ttggttgaag ctttgtactt ggtttgtggt    60
gaaagaggtt agttttacac tccaaagact                                      90

<210> SEQ ID NO 13
<211> LENGTH: 261
<212> TYPE: DNA
<213> ORGANISM: HomoSapiens

<400> SEQUENCE: 13
tttgtgaacc aacacctgtg cggctcacac ctggtggaag ctctctacct agtgtgcggg    60
gaacgaggct agttctacac acccaagacc cgccgggagg cagaggacct gcaggtgggg   120
caggtggagc tgggcggcgg ccctggtgca ggcagcctgc agcccttggc cctggagggg   180
tccctgcaga agcgtggcat tgtggaacaa tgctgtacca gcatctgctc cctctaccag   240
ctggagaact actgcaacta g                                             261

<210> SEQ ID NO 14
<211> LENGTH: 261
<212> TYPE: DNA
<213> ORGANISM: HomoSapiens

<400> SEQUENCE: 14
tttgttaacc aacatttgtg tggttctcat ttggttgaag ctttgtactt ggtttgtggt    60
gaaagaggtt agttttacac tccaaagact agaagagaag ctgaagattt gcaagttggt   120
caagttgaat tgggtggtgg tccaggtgct ggttctttgc aaccattggc tttggaaggt   180
tctttgcaaa agagaggtat tgttgaacaa tgttgtactt ctatttgttc tttgtaccaa   240
ttggaaaact actgtaacta a                                             261

<210> SEQ ID NO 15
<211> LENGTH: 22
<212> TYPE: PRT
<213> ORGANISM: HomoSapiens

<400> SEQUENCE: 15

Phe Val Asn Gln His Leu Cys Gly Ser His Leu Val Glu Ala Leu Tyr
1               5                   10                  15

Leu Val Cys Gly Glu Arg
            20

<210> SEQ ID NO 16
<211> LENGTH: 8
<212> TYPE: PRT
<213> ORGANISM: HomoSapiens
<220> FEATURE:
<221> NAME/KEY: MISC_FEATURE
<222> LOCATION: (4)..(4)
<223> OTHER INFORMATION: Xaa=F-Phe

<400> SEQUENCE: 16

Gly Phe Phe Xaa Thr Lys Pro Thr
1               5
```